(12) United States Patent
Johnston et al.

(10) Patent No.: US 8,858,659 B2
(45) Date of Patent: *Oct. 14, 2014

(54) PROCESSES FOR PRODUCING DENATURED ETHANOL

(75) Inventors: Victor J. Johnston, Houston, TX (US); Lincoln Sarager, Houston, TX (US); R. Jay Warner, Houston, TX (US); Heiko Weiner, Pasadena, TX (US); Trinity Horton, Houston, TX (US); Radmila Jevtic, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 741 days.

This patent is subject to a terminal disclaimer.

(21) Appl. No.: 12/889,260

(22) Filed: Sep. 23, 2010

(65) Prior Publication Data

US 2011/0185628 A1    Aug. 4, 2011

Related U.S. Application Data

(60) Provisional application No. 61/300,815, filed on Feb. 2, 2010, provisional application No. 61/332,727, filed on May 7, 2010, provisional application No. 61/332,696, filed on May 7, 2010.

(51) Int. Cl.
*C10L 1/182* (2006.01)
*C09K 3/00* (2006.01)
(Continued)

(52) U.S. Cl.
CPC .............. *C07C 29/149* (2013.01); *C10L 1/10* (2013.01); *C10L 1/182* (2013.01); *C09K 3/00*
(Continued)

(58) Field of Classification Search
USPC .................. 568/885, 880, 881, 884; 260/638; 44/451; 252/182.12, 364; 518/700
See application file for complete search history.

(56) References Cited

U.S. PATENT DOCUMENTS 1,939,116 A    12/1933 Fuchs
2,105,540 A    1/1938 Lazier
(Continued)

FOREIGN PATENT DOCUMENTS

CN    1230458    10/1999
CN    102091429    6/2011
(Continued)

OTHER PUBLICATIONS

Zheng, et al., (2007). Preparation and catalytic properties of a bimetallic Sn—Pt complex in the supercages of NaY zeolite by use of surface organometallic chemistry, Applied Organometallic Chemistry, 21(10), 836-840.
(Continued)

*Primary Examiner* — James Goloboy
*Assistant Examiner* — Chantel Graham

(57) ABSTRACT

In one embodiment, the invention is to a process for producing a denatured ethanol composition comprising the steps of hydrogenating an acetic acid feed in the presence of a catalyst to form a crude ethanol product comprising ethanol, and at least one denaturant and separating the crude ethanol product in one or more separation units into a denatured ethanol composition and one or more derivative streams. The denatured ethanol composition comprises from 0.01 wt. % to 40 wt % denaturant, based on the total weight of the denatured ethanol composition.

32 Claims, 4 Drawing Sheets

(51) Int. Cl.

| | | |
|---|---|---|
| C10L 1/10 | (2006.01) | |
| C07C 29/149 | (2006.01) | |
| C07C 45/48 | (2006.01) | |
| C07B 61/00 | (2006.01) | |
| C07C 27/06 | (2006.01) | |
| C10L 1/185 | (2006.01) | |
| C10L 1/02 | (2006.01) | |
| C07C 29/84 | (2006.01) | |
| C10L 1/12 | (2006.01) | |
| C10L 1/19 | (2006.01) | |
| C10L 1/16 | (2006.01) | |
| C07C 45/41 | (2006.01) | |
| C10L 1/188 | (2006.01) | |
| C07C 49/08 | (2006.01) | |

(52) U.S. Cl.
CPC ........ (2013.01); *C07C 45/48* (2013.01); *C07B 61/00* (2013.01); *C10L 1/1824* (2013.01); *C07C 27/06* (2013.01); *C10L 1/1857* (2013.01); *C10L 1/023* (2013.01); *C07C 29/84* (2013.01); *C10L 1/02* (2013.01); *C10L 1/125* (2013.01); *C10L 1/19* (2013.01); *C10L 1/1616* (2013.01); *C07C 45/41* (2013.01); *C10L 1/1881* (2013.01); *C10L 1/026* (2013.01); *C07C 49/08* (2013.01)
USPC ........................ 44/451; 252/182.12; 252/364

(56) References Cited

U.S. PATENT DOCUMENTS

| | | |
|---|---|---|
| 2,108,133 A | 2/1938 | McCall |
| 2,192,137 A | 2/1940 | Kvalnes |
| 2,549,416 A | 4/1951 | Brooks |
| 2,607,807 A | 8/1952 | Ford |
| 2,649,407 A | 8/1953 | Harrison et al. |
| 2,702,783 A | 2/1955 | Harrison et al. |
| 2,744,939 A | 5/1956 | Kennel |
| 2,801,209 A | 7/1957 | Muller et al. |
| 2,882,244 A | 4/1959 | Milton |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Adam et al. |
| 3,702,886 A | 11/1972 | Argauer et al. |
| 3,729,429 A | 4/1973 | Robson |
| 3,769,329 A | 10/1973 | Knox et al. |
| 3,847,756 A | 11/1974 | Statman et al. |
| 3,953,524 A | 4/1976 | Steiner |
| 3,990,952 A | 11/1976 | Katzen et al. |
| 4,052,467 A | 10/1977 | Mills et al. |
| 4,065,512 A | 12/1977 | Cares |
| 4,270,015 A | 5/1981 | Knifton et al. |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulprathipanja et al. |
| 4,328,373 A | 5/1982 | Strojny |
| 4,337,351 A | 6/1982 | Larkins |
| 4,379,028 A | 4/1983 | Berg et al. |
| 4,395,576 A | 7/1983 | Kwantes et al. |
| 4,398,039 A | 8/1983 | Pesa et al. |
| 4,399,305 A | 8/1983 | Schreck et al. |
| 4,421,939 A | 12/1983 | Kiff et al. |
| 4,422,903 A | 12/1983 | Messick et al. |
| 4,426,541 A | 1/1984 | King |
| 4,443,639 A | 4/1984 | Pesa et al. |
| 4,451,677 A | 5/1984 | Bradley et al. |
| 4,454,358 A | 6/1984 | Kummer et al. |
| 4,465,854 A | 8/1984 | Pond et al. |
| 4,465,875 A | 8/1984 | Greenbank et al. |
| 4,471,136 A | 9/1984 | Larkins et al. |
| 4,480,115 A | 10/1984 | McGinnis |
| 4,492,808 A | 1/1985 | Hagen et al. |
| 4,497,967 A | 2/1985 | Wan |
| 4,514,515 A | 4/1985 | Travers et al. |
| 4,517,391 A | 5/1985 | Schuster et al. |
| 4,520,213 A | 5/1985 | Victor |
| 4,521,630 A | 6/1985 | Wattimena et al. |
| 4,527,995 A | 7/1985 | Itow et al. |
| 4,541,897 A | 9/1985 | Sommer et al. |
| 4,550,185 A | 10/1985 | Mabry et al. |
| 4,559,109 A | 12/1985 | Lee et al. |
| 4,569,726 A | 2/1986 | Berg et al. |
| 4,581,473 A | 4/1986 | Polichnowski et al. |
| 4,592,806 A | 6/1986 | Ilgner et al. |
| 4,613,700 A | 9/1986 | Maki et al. |
| 4,626,321 A | 12/1986 | Grethlein et al. |
| 4,626,604 A | 12/1986 | Hiles et al. |
| 4,678,543 A | 7/1987 | Houben et al. |
| 4,692,218 A | 9/1987 | Houben et al. |
| 4,696,596 A | 9/1987 | Russell |
| 4,760,171 A | 7/1988 | Isogal et al. |
| 4,762,817 A | 8/1988 | Logsdon et al. |
| 4,777,303 A | 10/1988 | Kitson et al. |
| 4,804,791 A | 2/1989 | Kitson et al. |
| 4,826,795 A | 5/1989 | Kitson et al. |
| 4,842,693 A | 6/1989 | Wheldon |
| 4,876,402 A | 10/1989 | Logsdon et al. |
| 4,886,905 A | 12/1989 | Larkins |
| 4,961,826 A | 10/1990 | Grethlein et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,004,845 A | 4/1991 | Bradley et al. |
| 5,008,235 A | 4/1991 | Wegman et al. |
| 5,026,908 A | 6/1991 | Smith et al. |
| 5,035,776 A | 7/1991 | Knapp |
| 5,061,671 A | 10/1991 | Kitson et al. |
| 5,070,016 A | 12/1991 | Hallberg et al. |
| 5,093,534 A | 3/1992 | Ludwig et al. |
| 5,124,004 A | 6/1992 | Grethlein et al. |
| 5,137,861 A | 8/1992 | Shih et al. |
| 5,144,068 A | 9/1992 | Smith et al. |
| 5,149,680 A | 9/1992 | Kitson et al. |
| 5,155,084 A | 10/1992 | Horn et al. |
| 5,185,481 A | 2/1993 | Muto et al. |
| 5,206,434 A | 4/1993 | Scates et al. |
| 5,215,902 A | 6/1993 | Tedder |
| 5,233,099 A | 8/1993 | Tabata et al. |
| 5,237,108 A | 8/1993 | Marraccini et al. |
| 5,241,106 A | 8/1993 | Inoue et al. |
| 5,243,095 A | 9/1993 | Roberts et al. |
| 5,250,271 A | 10/1993 | Horizoe et al. |
| 5,284,983 A | 2/1994 | Muto et al. |
| 5,306,845 A | 4/1994 | Yokohama et al. |
| 5,334,769 A | 8/1994 | Ferrero et al. |
| 5,348,625 A | 9/1994 | Berg |
| 5,350,504 A | 9/1994 | Dessau |
| 5,399,752 A | 3/1995 | Okrasinski et al. |
| 5,415,741 A | 5/1995 | Berg |
| 5,426,246 A | 6/1995 | Nagahara et al. |
| 5,437,770 A | 8/1995 | Berg |
| 5,445,716 A | 8/1995 | Berg |
| 5,449,440 A | 9/1995 | Rescalli et al. |
| 5,475,144 A | 12/1995 | Watson et al. |
| 5,476,827 A | 12/1995 | Ferrero et al. |
| 5,480,665 A | 1/1996 | Smith |
| 5,488,185 A | 1/1996 | Ramachandran et al. |
| 5,502,248 A | 3/1996 | Funk et al. |
| 5,527,969 A | 6/1996 | Kaufhold et al. |
| 5,565,068 A | 10/1996 | Parker et al. |
| RE35,377 E | 11/1996 | Steinberg et al. |
| 5,585,523 A | 12/1996 | Weiguny et al. |
| 5,599,976 A | 2/1997 | Scates et al. |
| 5,663,430 A | 9/1997 | Morris et al. |
| 5,720,784 A | 2/1998 | Killick et al. |
| 5,762,765 A | 6/1998 | Berg |
| 5,767,307 A | 6/1998 | Ramprasad et al. |
| 5,770,770 A | 6/1998 | Kim et al. |
| 5,800,681 A | 9/1998 | Berg |
| 5,821,111 A | 10/1998 | Gaddy et al. |

(56) References Cited

U.S. PATENT DOCUMENTS

| | | |
|---|---|---|
| 5,849,657 A | 12/1998 | Rotgerink et al. |
| 5,858,031 A | 1/1999 | Perlman |
| 5,861,530 A | 1/1999 | Atkins et al. |
| 5,945,570 A | 8/1999 | Arhancet et al. |
| 5,955,397 A | 9/1999 | Didillon et al. |
| 5,973,193 A | 10/1999 | Crane et al. |
| 5,993,610 A | 11/1999 | Berg |
| 6,040,474 A | 3/2000 | Jobson et al. |
| 6,049,008 A | 4/2000 | Roberts et al. |
| 6,093,845 A | 7/2000 | Van Acker et al. |
| 6,114,571 A | 9/2000 | Abel et al. |
| 6,121,498 A | 9/2000 | Tustin et al. |
| 6,140,535 A | 10/2000 | Williams |
| 6,143,930 A | 11/2000 | Singh et al. |
| 6,232,352 B1 | 5/2001 | Vidalin |
| 6,232,504 B1 | 5/2001 | Barteau et al. |
| 6,294,703 B1 | 9/2001 | Hara et al. |
| 6,375,807 B1 | 4/2002 | Nieuwoudt et al. |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,509,290 B1 | 1/2003 | Vaughn et al. |
| 6,559,333 B1 | 5/2003 | Brunelle et al. |
| 6,603,038 B1 | 8/2003 | Hagemeyer et al. |
| 6,627,770 B1 | 9/2003 | Cheung et al. |
| 6,632,330 B1 | 10/2003 | Colley et al. |
| 6,657,078 B2 | 12/2003 | Scates et al. |
| 6,685,754 B2 | 2/2004 | Kindig et al. |
| 6,693,213 B1 | 2/2004 | Kolena et al. |
| 6,696,596 B1 | 2/2004 | Herzog et al. |
| 6,723,886 B2 | 4/2004 | Allison et al. |
| 6,727,380 B2 | 4/2004 | Ellis et al. |
| 6,765,110 B2 | 7/2004 | Warner et al. |
| 6,768,021 B2 | 7/2004 | Horan et al. |
| 6,809,217 B1 | 10/2004 | Colley et al. |
| 6,812,372 B2 | 11/2004 | Janssen et al. |
| 6,852,877 B1 | 2/2005 | Zeyss et al. |
| 6,903,045 B2 | 6/2005 | Zoeller et al. |
| 6,906,228 B2 | 6/2005 | Fischer et al. |
| 6,927,048 B2 | 8/2005 | Verser et al. |
| 7,005,541 B2 | 2/2006 | Cheung et al. |
| 7,074,603 B2 | 7/2006 | Verser et al. |
| 7,084,312 B1 | 8/2006 | Huber et al. |
| 7,115,772 B2 | 10/2006 | Picard et al. |
| 7,208,624 B2 | 4/2007 | Scates et al. |
| 7,297,236 B1 | 11/2007 | van der Griend |
| 7,351,559 B2 | 4/2008 | Verser et al. |
| 7,375,049 B2 | 5/2008 | Hayes et al. |
| 7,399,892 B2 | 7/2008 | Rix et al. |
| 7,425,657 B1 | 9/2008 | Elliott et al. |
| 7,507,562 B2 | 3/2009 | Verser et al. |
| 7,538,060 B2 | 5/2009 | Barnicki et al. |
| 7,553,397 B1 | 6/2009 | Colley et al. |
| 7,572,353 B1 | 8/2009 | van der Griend |
| 7,601,865 B2 | 10/2009 | Verser et al. |
| 7,608,744 B1 | 10/2009 | Johnston et al. |
| 7,678,940 B2 | 3/2010 | Miura et al. |
| 7,682,812 B2 | 3/2010 | Verser et al. |
| 7,700,814 B2 | 4/2010 | Garton et al. |
| 7,718,039 B2 | 5/2010 | Dirkzwager et al. |
| 7,732,173 B2 | 6/2010 | Mairal et al. |
| 7,744,727 B2 | 6/2010 | Blum et al. |
| 7,816,565 B2 | 10/2010 | Johnston et al. |
| 7,820,852 B2 | 10/2010 | Johnston et al. |
| 7,834,223 B2 | 11/2010 | Atkins et al. |
| 7,842,844 B2 | 11/2010 | Atkins |
| 7,855,303 B2 | 12/2010 | Johnston et al. |
| 7,863,489 B2 | 1/2011 | Johnston et al. |
| 7,884,253 B2 | 2/2011 | Stites et al. |
| 7,888,082 B2 | 2/2011 | Verser et al. |
| 7,947,746 B2 | 5/2011 | Daniel et al. |
| 8,071,821 B2 | 12/2011 | Johnston et al. |
| 2003/0004057 A1 | 1/2003 | Yamaguchi et al. |
| 2003/0013908 A1 | 1/2003 | Horan et al. |
| 2003/0077771 A1 | 4/2003 | Verser et al. |
| 2003/0104587 A1 | 6/2003 | Verser et al. |
| 2003/0114719 A1 | 6/2003 | Fischer et al. |
| 2003/0191020 A1 | 10/2003 | Bhardwaj et al. |
| 2004/0195084 A1 | 10/2004 | Hetherington et al. |
| 2005/0028435 A1 | 2/2005 | Pace et al. |
| 2005/0176996 A1 | 8/2005 | Law et al. |
| 2006/0019360 A1 | 1/2006 | Verser et al. |
| 2006/0102520 A1 | 5/2006 | Lapinski et al. |
| 2006/0106246 A1 | 5/2006 | Warner et al. |
| 2006/0127999 A1 | 6/2006 | Verser et al. |
| 2007/0031954 A1 | 2/2007 | Mairal et al. |
| 2007/0238906 A1 | 10/2007 | Brown et al. |
| 2007/0270511 A1 | 11/2007 | Melnichuk et al. |
| 2008/0135396 A1 | 6/2008 | Blum |
| 2008/0193989 A1 | 8/2008 | Verser et al. |
| 2008/0207953 A1 | 8/2008 | Houssin et al. |
| 2009/0005588 A1 | 1/2009 | Hassan et al. |
| 2009/0014313 A1 | 1/2009 | Lee et al. |
| 2009/0023192 A1 | 1/2009 | Verser et al. |
| 2009/0069609 A1 | 3/2009 | Kharas et al. |
| 2009/0081749 A1 | 3/2009 | Verser et al. |
| 2009/0166172 A1 | 7/2009 | Casey |
| 2009/0209786 A1 | 8/2009 | Scates et al. |
| 2009/0221725 A1 | 9/2009 | Chornet et al. |
| 2009/0274480 A1 | 11/2009 | Zona |
| 2009/0281354 A1 | 11/2009 | Mariansky et al. |
| 2009/0318573 A1 | 12/2009 | Stites et al. |
| 2009/0326080 A1 | 12/2009 | Chornet et al. |
| 2010/0016454 A1 | 1/2010 | Gracey et al. |
| 2010/0029980 A1 | 2/2010 | Johnston et al. |
| 2010/0029993 A1 | 2/2010 | Johnston et al. |
| 2010/0029995 A1 | 2/2010 | Johnston et al. |
| 2010/0029996 A1 | 2/2010 | Danjo et al. |
| 2010/0030001 A1 | 2/2010 | Chen et al. |
| 2010/0030002 A1 | 2/2010 | Johnston et al. |
| 2010/0069514 A1 | 3/2010 | Gracey et al. |
| 2010/0069515 A1 | 3/2010 | Tirowidjojo et al. |
| 2010/0113843 A1 | 5/2010 | Lee et al. |
| 2010/0121114 A1 | 5/2010 | Weiner et al. |
| 2010/0125148 A1 | 5/2010 | Johnston et al. |
| 2010/0137630 A1 | 6/2010 | Garton et al. |
| 2010/0168467 A1 | 7/2010 | Johnston et al. |
| 2010/0168493 A1 | 7/2010 | Le Peltier et al. |
| 2010/0185021 A1 | 7/2010 | Ross et al. |
| 2010/0196789 A1 | 8/2010 | Fisher et al. |
| 2010/0197485 A1 | 8/2010 | Johnston et al. |
| 2010/0197959 A1 | 8/2010 | Johnston et al. |
| 2010/0197985 A1 | 8/2010 | Johnston et al. |
| 2010/0249479 A1 | 9/2010 | Berg-Slot et al. |
| 2011/0004033 A1 | 1/2011 | Johnston et al. |
| 2011/0046421 A1 | 2/2011 | Daniel et al. |
| 2011/0071312 A1 | 3/2011 | Johnston et al. |
| 2011/0082322 A1 | 4/2011 | Jevtic et al. |
| 2011/0098513 A1 | 4/2011 | Weiner et al. |
| 2011/0190547 A1 | 8/2011 | Jevtic et al. |
| 2011/0190548 A1 | 8/2011 | Jevtic et al. |
| 2011/0237837 A1 | 9/2011 | Al-Rabiah et al. |
| 2011/0275862 A1 | 11/2011 | Johnston et al. |

FOREIGN PATENT DOCUMENTS

| | | |
|---|---|---|
| CN | 102228831 | 11/2011 |
| CN | 102229520 | 11/2011 |
| DE | 2723611 | 11/1978 |
| DE | 3221077 | 12/1983 |
| EP | 0056488 | 7/1982 |
| EP | 0167300 A1 | 1/1986 |
| EP | 0137749 A2 | 2/1986 |
| EP | 0175558 A1 | 3/1986 |
| EP | 0104197 | 5/1986 |
| EP | 0192587 | 8/1986 |
| EP | 0253540 | 1/1988 |
| EP | 0372847 A2 | 6/1990 |
| EP | 0400904 | 12/1990 |
| EP | 0408528 | 1/1991 |
| EP | 0198682 B1 | 3/1991 |
| EP | 0285420 B1 | 5/1991 |

(56) References Cited

FOREIGN PATENT DOCUMENTS

| | | |
|---|---|---|
| EP | 0456647 | 11/1991 |
| EP | 0539274 | 4/1993 |
| EP | 0285786 B1 | 5/1993 |
| EP | 0557786 | 9/1993 |
| EP | 0953560 A1 | 11/1999 |
| EP | 0990638 | 4/2000 |
| EP | 0992482 | 4/2000 |
| EP | 0992484 | 4/2000 |
| EP | 1262234 | 12/2002 |
| EP | 1277826 | 1/2003 |
| EP | 2060553 A1 | 5/2009 |
| EP | 2060555 A1 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| GB | 745946 | 3/1956 |
| GB | 1168785 | 10/1969 |
| GB | 1559540 | 1/1980 |
| GB | 2136704 | 9/1984 |
| JP | 4-193304 | 7/1992 |
| JP | 6-116182 | 4/1994 |
| JP | 10-306047 A | 11/1998 |
| JP | 11-147845 | 6/1999 |
| JP | 2001-046874 A | 2/2001 |
| JP | 2001-157841 A | 6/2001 |
| JP | 2010-159212 | 7/2010 |
| WO | WO 83/03409 A1 | 10/1983 |
| WO | WO 03/040037 A1 | 5/2003 |
| WO | WO 03/106396 | 12/2003 |
| WO | WO 2007/003897 | 1/2007 |
| WO | WO 2007/145490 | 12/2007 |
| WO | WO 2008/098254 | 8/2008 |
| WO | WO 2008/135192 | 11/2008 |
| WO | WO 2009/009322 A1 | 1/2009 |
| WO | WO 2009/009323 A1 | 1/2009 |
| WO | WO 2009/048335 | 4/2009 |
| WO | WO 2009/063176 A1 | 5/2009 |
| WO | WO 2009/105860 A1 | 9/2009 |
| WO | WO 2010/014145 | 2/2010 |
| WO | WO 2010/014146 | 2/2010 |
| WO | WO 2010/014148 | 2/2010 |
| WO | WO 2010/014151 A1 | 2/2010 |
| WO | WO 2010/014152 | 2/2010 |
| WO | WO 2010/014153 A2 | 2/2010 |
| WO | WO 2010/056299 | 5/2010 |
| WO | WO 2010/055285 | 7/2010 |
| WO | WO 2011/053365 | 5/2011 |
| WO | WO 2011/097227 | 8/2011 |

OTHER PUBLICATIONS

ZeaChem, Inc., Technology Overview, Lakewood, Colorado www.zeachem.com, 2008.

Santori et al., (2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Pestman et al., Identification of the Active Sites in the Selective Hydrogenation of Acetic Acid to Acetaldehyde on Iron Oxide Catalysts, Journal of Catalysis 174:142-152 (1998).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Ordóñez et al., The role of metal and support sites on the hydrogenation of acetic acid on Ru-based catalysts, 21st NAM San Francisco, CA, Jun. 10, 2009.

Brunauer Emmett and Teller, J. Am. Chem. Soc. 60, 309 (1938).

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at < http://www.nacatsoc.org/20nam/abstracts/O-S9-18.pdf>.

Acala, et al., (2005). Experimental and DFT studies of the conversion of ethanol and acetic acid on PtSn-based catalysts, Journal of Physical Chemistry, 109(6), 2074-2085.

International Search Report and Written Opinion for PCT/US2009/004197 mailed Mar. 24, 2010 (14 pages).

International Search Report and Written Opinion for PCT/US2009/004195 mailed Mar. 26, 2010 (12 pages).

International Search Report and Written Opinion for PCT/US2010/022947 mailed Jun. 7, 2010.

International Preliminary Report on Patentability for PCT/US2011/023322 mailed Jun. 27, 2012.

Office Action for U.S. Appl. No. 13/273,054, filed Jun. 20, 2012.

International Fuel Quality Center Hart Downstream Energy Services: "Setting a Quality Standard for Fuel-Ethanol—DEH Ethanol Standard 18/2004 Report", Jan. 1, 2004, pp. 1-56.

International Search Report and Written Opinion for PCT/US2011/046507 mailed Aug. 13, 2012.

International Search Report and Written Opinion for PCT/US2011/023322 mailed Sep. 6, 2011.

Written Opinion mailed May 8, 2012 in corresponding International Application No. PCT/US2011/023322.

Zhang et al., Hydrogenation of Ethyl Acetate to Ethanol over Ni-Based Catalysts Obtained from Ni/Al Hydrotalcite-Like Compounds. Molecules 2010, 15, 5139-5152, 2010.

Pestman et al., The formation of ketones and aldehydes from carboxylic acids, structure-activity relationship for two competitive reactions, Journal of Molecular Catalysis A: Chemical 103 Jun. 14, 1995, 175-180.

Pestman et al., Reactions of Carboxylic Acids on Oxides, Journal of Catalysis 168:255-264 (1997).

Waterland, et al., "Safety and Performance Assessment of Ethanol/Diesel Blends (e-blend)", NREL/SR-540-34817, at p. 1-1, Sep. 2003.

J. Jones, et al., Platinum Metals Review, vol. 44, No. 3, pp. 94-104 (Jul. 2000).

Invitation to Pay Additional Fees and Partial Search Report for PCT/US2011/023331 mailed May 4, 2011.

International Search Report and Written Opinion for PCT/US2010/054136 mailed May 25, 2010.

International Search Report and Written Opinion for PCT/US2011/023338 mailed Sep. 6, 2011.

International Search Report for PCT/US2011/023269 mailed Aug. 25, 2010.

International Search Report for PCT/US2011/046508 dated Mar. 29, 2012.

International Search Report for PCT/US2011/046500 dated Mar. 29, 2012.

Invitation to Pay Fees for PCT/US2011/046493 dated Feb. 6, 2012.

Yamada, et al., J. of Mol. Catalysis; Chem.; 2011, 346, pp. 79-86.

500

PROCESSES FOR PRODUCING DENATURED ETHANOL

CROSS REFERENCE TO RELATED APPLICATIONS

This application claims priority to U.S. Provisional Application No. 61/300,815, filed on Feb. 2, 2010, U.S. Provisional Application No 61/332,727, filed on May 7, 2010, and U.S. Provisional Application No. 61/332,696, the entireties of which are incorporated herein by reference.

FIELD OF THE INVENTION

The present invention relates generally to processes for producing a denatured ethanol composition and, in particular, to processes for producing a denatured ethanol composition via the hydrogenation of acetic acid, which forms a crude ethanol product and a denaturant.

BACKGROUND OF THE INVENTION

Ethanol is often produced for and utilized as a component in various consumable products, e.g., beer, wine, and spirits. Typically, ethanol intended for such uses is produced via fermentation. Many government agencies impose high duties or taxes on consumable ethanol, thereby increasing the cost to consumers.

There are, however, many other uses for ethanol that do not involve consumption, e.g., fuels, chemical solvents, or pharmaceuticals. As such, in an effort to provide inexpensive ethanol for non-consumable uses, the duties or taxes imposed on consumable ethanol are typically not required for ethanol that is not intended to be consumed. To ensure that such ethanol compositions are used for non-consumable applications, most countries have laws and regulations requiring that these ethanol compositions include a denaturant, which is added to an otherwise substantially pure ethanol composition in order to render the ethanol non-potable. Thus, ethanol compositions that include a denaturant and which are not intended for consumption are commonly referred to as "denatured ethanol" or "denatured alcohol." Conventional denaturants include methanol, isopropyl alcohol, acetone, methyl ethyl ketone, ethyl acetate, methyl isobutyl ketone, and acetaldehyde.

The processing step of adding a denaturant to an otherwise potable ethanol composition adds complication and cost to in conventional processes for forming denatured ethanol. Thus, the need exists for new and improved processes for forming denatured ethanol.

SUMMARY OF THE INVENTION

In a first embodiment, the present invention is directed to a process for producing a denatured ethanol composition, the process comprising hydrogenating acetic acid in the presence of a catalyst to form a crude ethanol product comprising ethanol, and at least one denaturant; separating the crude ethanol product in one or more separation units into a denatured ethanol composition and one or more derivative streams, wherein the denatured ethanol composition, as formed, comprises from 0.01 wt. % to 40 wt % denaturant, based on the total weight of the denatured ethanol composition.

In a second embodiment, the present invention is directed to a process for producing a denatured ethanol composition, the process comprising hydrogenating acetic acid in the presence of a catalyst to form a crude ethanol product comprising ethanol and a denaturant; separating the crude ethanol product into an ethanol stream and at least one derivative stream comprising separated denaturant; further purifying the ethanol stream to form a purified ethanol stream; and combining at least a portion of the separated denaturant with the purified ethanol stream to produce the denatured ethanol composition.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1A:
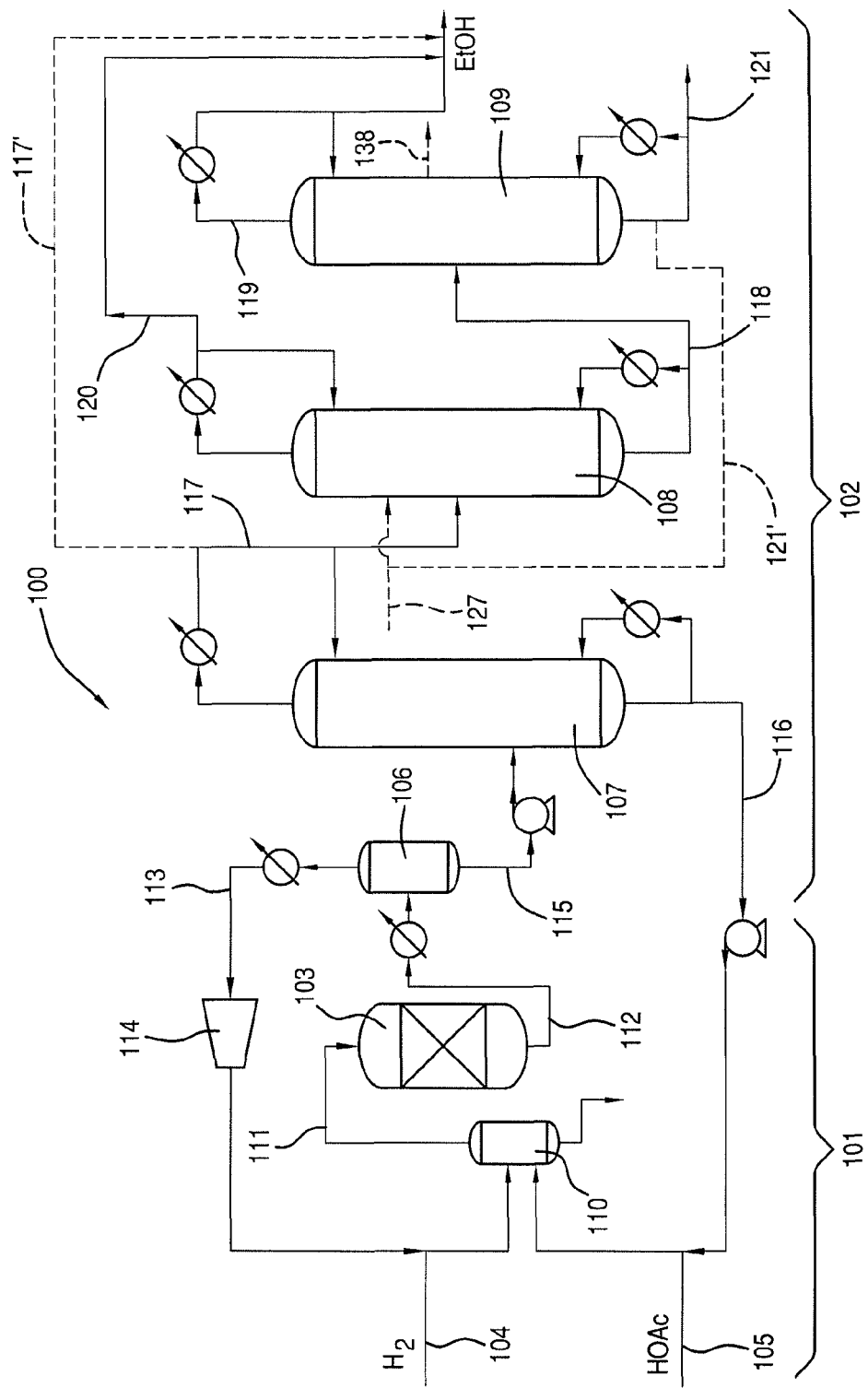
FIG. 1A is a schematic diagram of a hydrogenation system in accordance with one embodiment of the present invention.

Conventional denatured ethanol preparation processes begin with the production of a purified ethanol. In these processes, ethanol may be formed and subsequently purified by conventional methods. A denaturant is then added to the purified ethanol to form the denatured ethanol.

The present invention relates to processes for producing denatured ethanol compositions. In one embodiment, the invention is to a process comprising the steps of hydrogenating acetic acid, e.g., in the presence of a catalyst, to form a crude ethanol product. The crude ethanol product comprises at least one, e.g., at least two or at least three, denaturant(s) In one embodiment, the denaturant(s) may be co-produced with the ethanol. In another embodiment, the denaturant(s) are formed as a by-product of the hydrogenation reaction. In other words, the denaturant is formed in situ with the ethanol. The processes of the present invention, in one embodiment, further comprise separating the crude ethanol product into a denatured ethanol composition and one or more derivative streams. The separating may be performed in one or more, e.g., two or more, or three or more, separation units, e.g., distillation columns. The resultant denatured ethanol composition, as formed, is derived from acetic acid and comprises from 0.01 wt. % to 40 wt. % denaturant, e.g., from 0.01 wt. % to 25 wt. %, from 0.01 wt. % to 20 wt. %, or from 1 wt. % to 15 wt. %, and from 50 wt. % to 99 wt. % ethanol, e.g., from 60 wt. % to 99 wt. % or from 70 wt. % to 95 wt. %, based on the total weight of the denatured ethanol composition. Thus, by forming the denaturant in situ along with the ethanol in the hydrogenation step, the inventive processes may produce denatured ethanol more efficiently and may reduce processing steps. In particular, the processes of the present invention may eliminate the need for separately producing or obtaining a denaturant and subsequently adding the denaturant to ethanol.

In another embodiment, the invention is to a process for producing a denatured ethanol composition where the denaturant is formed from the hydrogenation of acetone, which may be added to the reaction zone or formed as an intermediate in situ as a by-product from acetic acid hydrogenation. In one aspect, for example, the process comprises the step of contacting acetic acid and acetone to form an acetic acid reaction mixture. The process further comprises hydrogenating the acetic acid reaction mixture in the presence of a catalyst to form a crude ethanol product comprising ethanol and isopropanol. In one embodiment, the acetone is formed in an auxiliary acetone reactor or is obtained from an external source. Once formed or obtained, the acetone may be contacted with the acetic acid as discussed above. In another aspect, the catalyst or reaction conditions employed in the hydrogenation reaction are selected such that acetone is formed as a by-product of the acetic acid hydrogenation reaction. Once formed, the acetone intermediate may be hydrogenated to form isopropanol denaturant. In these embodiments, the ethanol is co-produced with the isopropanol denaturant. Preferably, the ethanol and the isopropanol are produced in the same reactor. The processes of the present invention, in one embodiment, further comprise separating the crude ethanol product into a denatured ethanol composition and one or more derivative streams. The resultant denatured ethanol composition, as formed, comprises from 0.01 wt. % to 10 wt. % isopropanol denaturant, e.g., from 0.01 wt. % to 5 wt. %, or from 0.01 wt. % to 3 wt. %, and from 50 wt. % to 99 wt. % ethanol, e.g., from 60 wt. % to 99 wt. % or from 70 wt. % to 95 wt. %, based on the total weight of the denatured ethanol composition.

Hydrogenation Process

The hydrogenation of acetic acid to form ethanol and water may be represented by the following reaction:

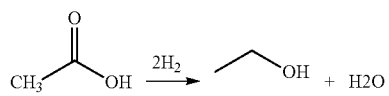

Suitable hydrogenation catalysts include catalysts comprising a first metal and optionally one or more of a second metal, a third metal or additional metals, optionally on a catalyst support. The first and optional second and third metals may be selected from Group IB, IIB, IIIB, IVB, VB, VIB, VIIB, VIII transitional metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, silver/palladium, copper/palladium, nickel/palladium, gold/palladium, ruthenium/rhenium, and ruthenium/iron. Exemplary catalysts are further described in U.S. Pat. No. 7,608,744 and U.S. Publication Nos. 2010/0029995 and 2010/0197485, the entireties of which are incorporated herein by reference.

In one exemplary embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. When the first metal comprises platinum, it is preferred that the catalyst comprises platinum in an amount less than 5 wt. %, e.g., less than 3 wt. % or less than 1 wt. %, due to the high demand for platinum.

As indicated above, the catalyst optionally further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

If the catalyst includes two or more metals, e.g., a first metal and a second metal, the first metal optionally is present in the catalyst in an amount from 0.1 wt. % to 10 wt. %, e.g., from 0.1 wt. % to 5 wt. %, or from 0.1 wt. % to 3 wt. %. The second metal preferably is present in an amount from 0.1 wt. % and 20 wt. %, e.g., from 0.1 wt. % to 10 wt. %, or from 0.1 wt. % to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 wt. % and 4 wt. %, e.g., from 0.1 wt. % to 3 wt. %, or from 0.1 wt. % to 2 wt. %.

In addition to one or more metals, the exemplary catalysts further comprise a support or a modified support, meaning a support that includes a support material and a support modifier, which adjusts the acidity of the support material. The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that use a modified support, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

In the production of ethanol, the catalyst support may be modified with a support modifier. Preferably, the support modifier is a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group JIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. Preferably, the support modifier is a calcium silicate, and more preferably calcium metasilicate ($CaSiO_3$). If the support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain NorPro. The Saint-Gobain NorPro SS61138 silica contains approximately 95 wt. % high surface area silica; a surface area of about 250 $m^2/g$; a median pore diameter of about 12 nm; an average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 (Sud Chemie) silica spheres having a nominal diameter of about 5 mm, a density of about 0.562 g/ml, in absorptivity of about 0.583 g $H_2O$/g support, a surface area of about 160 to 175 $m^2/g$, and a pore volume of about 0.68 ml/g.

As will be appreciated by those of ordinary skill in the art, support materials are selected such that the catalyst system is suitably active, selective and robust under the process conditions employed for the formation of ethanol.

The metals of the catalysts may be dispersed throughout the support, coated on the outer surface of the support (egg shell) or decorated on the surface of the support.

The catalyst compositions suitable for use with the present invention preferably are formed through metal impregnation of the modified support, although other processes such as chemical vapor deposition may also be employed. Such impregnation techniques are described in U.S. Pat. No. 7,608,744, U.S. Publication No. 2010/0029995, and U.S. application Ser. No. 12/698,968, referred to above, the entireties of which are incorporated herein by reference.

Some embodiments of the process of hydrogenating acetic acid to form ethanol according to one embodiment of the invention may include a variety of configurations using a fixed bed reactor or a fluidized bed reactor, as one of skill in the art will readily appreciate. In many embodiments of the present invention, an "adiabatic" reactor can be used; that is, there is little or no need for internal plumbing through the reaction zone to add or remove heat. In other embodiments, radial flow reactor or reactors may be employed, or a series of reactors may be employed with or with out heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 KPa to 3000 KPa (about 1.5 to 435 psi), e.g., from 50 KPa to 2300 KPa, or from 100 KPa to 1500 KPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In term ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. As petroleum and natural gas prices fluctuate, becoming either more or less expensive, methods for producing acetic acid and intermediates such as methanol and carbon monoxide from alternate carbon sources have drawn increasing interest. In particular, when petroleum is relatively expensive compared to natural gas, it may become advantageous to produce acetic acid from synthesis gas ("syn gas") that is derived from any available carbon source. U.S. Pat. No. 6,232,352, the disclosure of which is incorporated herein by reference, for example, teaches a method of retrofitting a methanol plant for the manufacture of acetic acid. By retrofitting a methanol plant, the large capital costs associated with carbon monoxide generation for a new acetic acid plant are significantly reduced or largely eliminated. All or part of the syn gas is diverted from the methanol synthesis loop and supplied to a separator unit to recover carbon monoxide and hydrogen, which are then used to produce acetic acid. In addition to acetic acid, such a process can also be used to make hydrogen which may be utilized in connection with this invention.

Methanol carbonylation processes suitable for production of acetic acid are described in U.S. Pat. Nos. 7,208,624, 7,115,772, 7,005,541, 6,657,078, 6,627,770, 6,143,930, 5,599,976, 5,144,068, 5,026,908, 5,001,259, and 4,994,608, the disclosures of which are incorporated herein by reference. Optionally, the production of ethanol may be integrated with such methanol carbonylation processes.

U.S. Pat. No. RE 35,377 also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syn gas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas as well as U.S. Pat. No. 6,685,754, the disclosures of which are incorporated herein by reference.

In one optional embodiment, the acetic acid feed stream fed to the hydrogenation reaction comprises acetic acid and may also comprise other carboxylic acids, e.g., propionic acid, esters, and anhydrides, as well as acetaldehyde and acetone. In one embodiment, the acetic acid fed to the hydrogenation reaction comprises propionic acid. For example the propionic acid in the acetic acid feed stream may range from 0.001 wt. % to 15 wt. %, e.g., from 0.001 wt. % to 0.11 wt. %, from 0.125 wt. % to 12.5 wt. %, from 1.25 wt. % to 11.25, or from 3.75 wt. % to 8.75 wt. %. Thus, the acetic acid feed stream may be a cruder acetic acid feed stream, e.g., a less-refined acetic acid feed stream. In these embodiments, the propionic acid in the acetic acid feed stream is hydrogenated to form n-propanol, which may serve as a denaturant. The n-propanol may be present in the denatured ethanol composition an amount ranging from 0.001 wt. % to 15 wt. %, e.g., from 0.001 wt. % to 0.11 wt. %, 0.13 wt. % to 13.2 wt. %, from 1.3 wt. % to 11.9 wt. %, or from 4 wt. % to 9.3 wt. %.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

In one embodiment, acetone is added to the reactor as a reactant in addition to the acetic acid and hydrogen. Without being bound by theory, it is believed that the addition of acetone to the reaction provides for the production of isopropanol, which may serve as a denaturant. In another aspect, acetone is formed as a by-product of the hydrogenation of acetic acid. Once formed, the acetone may be hydrogenated to form isopropanol as denaturant. In some embodiments, where an isopropanol denaturant is desired, separate catalysts may be utilized to yield a higher concentration of acetone, which, upon subsequent hydrogenation, would result in a higher concentration of isopropanol in the crude ethanol composition. As an example, a catalyst composition comprising a support such as $TiO_2$, $ZrO_2$, $Fe_2O_3$, or $CeO_2$ may be used. Other exemplary catalyst compositions include ruthenium supported by $SiO_2$, iron supported by carbon, or palladium supported by carbon.

In one embodiment, the acetone is formed in an auxiliary reaction performed in an auxiliary acetone reactor. As an example, acetic acid may be reacted in the auxiliary reactor under conditions effective to form the acetone, e.g., ketonization. The acetic acid fed to the auxiliary reactor may be drawn from the acetic acid feed stream fed to the hydrogenation reactor. The auxiliary reactor may be of the types discussed above. For example, the auxiliary reactor may be a fixed bed reactor that has a catalyst disposed therein. Preferably, the auxiliary reactor is in the shape of a pipe or tube, where the reactants, typically in the vapor form, are passed over or through the catalyst, which is disposed in the pipe or tube. In some embodiments, the auxiliary reactor utilizes a catalyst that promotes ketonization and/or favors the production of acetone. As an example, the catalyst may comprise a basic catalyst, e.g., thorium oxide. In some embodiments, the acetone yielded by the auxiliary reactor is directed to the hydrogenation reactor as a reactant in addition to the acetic acid and the hydrogen.

The acetic acid may be vaporized at the reaction temperature, following which the vaporized acetic acid can be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment the acetic acid may be vaporized at the boiling point of acetic acid at the particular pressure, and then the vaporized acetic acid may be further heated to the reactor inlet temperature. In another embodiment, the acetic acid is transferred to the vapor state by passing hydrogen, recycle gas, another suitable gas, or mixtures thereof through the acetic acid at a temperature below the boiling point of acetic acid, thereby humidifying the carrier gas with acetic acid vapors, followed by heating the mixed vapors up to the reactor inlet temperature. Preferably, the acetic acid is transferred to the vapor by passing hydrogen and/or recycle gas through the acetic acid at a temperature at or below 125° C., followed by heating of the combined gaseous stream to the reactor inlet temperature.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 50 mole % of the converted acetic acid is converted to ethanol, we refer to the ethanol selectivity as 50%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are not detectable. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 200 grams of ethanol per kilogram catalyst per hour, e.g., at least 400 grams of ethanol per kilogram catalyst per hour or at least 600 grams of ethanol per kilogram catalyst per hour, is preferred. In terms of ranges, the productivity preferably is from 200 to 3,000 grams of ethanol per kilogram catalyst per hour, e.g., from 400 to 2,500 per kilogram catalyst per hour or from 600 to 2,000 per kilogram catalyst per hour.

In various embodiments, the crude ethanol product produced by the hydrogenation process, before any subsequent processing, such as purification and separation, will typically comprise unreacted acetic acid, ethanol, and water. As used herein, the term "crude ethanol product" refers to any composition comprising from 5 wt. % to 70 wt. % ethanol and from 5 wt. % to 35 wt. % water. In some exemplary embodiments, the crude ethanol product comprises ethanol in an amount from 5 wt. % to 70 wt. %, e.g., from 10 wt. % to 60 wt. %, or from 15 wt. % to 50 wt. %, based on the total weight of the crude ethanol product. Preferably, the crude ethanol product comprises at least 10 wt. % ethanol, at least 15 wt. % ethanol, or at least 20 wt. % ethanol.

The crude ethanol product typically will further comprise unreacted acetic acid, depending on conversion, for example, in an amount of less than 90 wt. %, e.g., less than 80 wt. % or less than 70 wt. %. In terms of ranges, the unreacted acetic acid is preferably present in amounts from 0 to 90 wt. %, e.g., from 5 wt. % to 80 wt. %, from 15 wt. % to 70 wt. %, from 20 wt. % to 70 wt. % or from 25 wt. % to 65 wt. %. Where acetone is included as a reactant, the crude ethanol product may comprise from 0.01 wt. % to 10 wt. % isopropanol, e.g., from 0.1 wt. % to 10 wt %, from 1 wt. % to 9 wt. % or from 3 wt. % to 7 wt. %. In other embodiments, the crude ethanol product comprises from 0.01 wt. % to 20 wt. % diethyl ether, e.g., from 0.1 wt. % to 10 wt. %, from 1 wt. % to 9 wt. % or from 3 wt. % to 7 wt. %. As water is formed in the reaction process, the crude ethanol product will generally comprise water, for example, in amounts ranging from 5 wt. % to 35 wt. %, e.g., from 10 wt. % to 30 wt. % or from 10 wt. % to 26 wt. %. Ethyl acetate may also be produced during the hydrogenation of acetic acid or through side reactions. In these embodiments, the crude ethanol product comprises ethyl acetate in amounts ranging from 0 to 20 wt. %, e.g., from 0 to 15 wt. %, from 1 to 12 wt. % or from 3 to 10 wt. %. Acetaldehyde may also be produced through side reactions. In these embodiments, the crude ethanol product comprises acetaldehyde in amounts ranging from 0 to 10 wt. %, e.g., from 0 to 3 wt. %, from 0.1 to 3 wt. % or from 0.2 to 2 wt. %. In some embodiments where propionic acid is included as a reactant, the n-propanol formed via hydrogenation may be present in the crude ethanol product an amount ranging from 0.001 wt. % to 15 wt. %, e.g., from 0.001 wt. % to 0.11 wt. %, 0.13 wt. % to 13.2 wt. %, from 1.3 wt. % to 11.9 wt. %, or from 4 wt. % to 9.3 wt. %.

Thus, the hydrogenation reaction produces a crude ethanol product that may comprise, inter alia, denaturants such as acetic acid, isopropanol, ethyl acetate, diethyl ether, acetaldehyde, and/or n-propanol. Each of these in situ-formed compounds, alone or in combination with one another, may serve as a denaturant in a denatured ethanol composition. In some embodiments, all or a portion of the crude ethanol product may be combined with a purified ethanol stream to form a denatured ethanol composition. It is within the scope of the invention to adjust the reaction parameters to achieve desired crude ethanol product and, thus, a desired denatured ethanol composition. In one embodiment, amount of reactants, e.g., acetic acid, acetone, and/or propionic acid, etc., fed to the hydrogenation reactor may be adjusted so as to achieve a specific amount of one or more components, e.g., denaturants, in the crude ethanol product. The denaturant, thus produced, may be combined with a purified ethanol stream to form a denatured ethanol composition. For example, a denatured ethanol composition comprising about 5 parts isopropanol to 100 parts ethanol, may be produced by feeding an acetic acid stream comprising acetic acid and acetone. As another example, a denatured ethanol composition comprising about 5 parts n-propanol to 100 parts ethanol, may be produced by feeding an acetic acid stream comprising acetic acid and propionic acid. It is further within the scope of the invention to adjust additional hydrogenation reactor parameters to achieve a crude ethanol product comprising a desired amount of a particular denaturant or combination of denaturants. For example, in order to produce a crude ethanol product comprising about 10 parts diethyl ether, a hydrogenation catalyst having an acidic support may be utilized as described in co-pending U.S. aplication Ser. No. 12/850,414, entitled "Processes for Making Diethyl Ether from Acetic Acid," filed on Aug. 4, 2010, the entire contents and disclosure of which is hereby incorporated by reference.

In one embodiment, because it is difficult to separate isopropanol and ethanol from one another, all or a portion of the isopropanol formed in the hydrogenation reaction may follow the ethanol through the separation scheme.

Because the crude ethanol composition, as formed, may contain in situ-formed denaturant(s), at least a portion of the crude ethanol composition, with or without further separation, may be combined with a purified ethanol stream to form a denatured ethanol composition. In one embodiment, one or more of the in situ-formed denaturants may be separated from the crude ethanol product and combined with a purified ethanol stream. In other embodiments, at least a portion, e.g., an aliquot portion, of the crude ethanol product may be combined with a purified ethanol stream. For example, when the crude ethanol product comprises n-propanol, at least a portion of an n-propanol-containing crude ethanol product may be combined with a purified ethanol stream to form a denatured ethanol composition comprising an n-propanol denaturant. In another embodiment, at least a portion of the n-propanol is separated from the crude ethanol product and combined with a purified ethanol stream to form an n-propanol denatured ethanol composition. As another example, where acetic acid is the desired denaturant, at least a portion of an acetic acid-containing crude ethanol composition may be combined with a purified ethanol stream to form a denatured ethanol composition comprising an acetic acid denaturant. In another embodiment, at least a portion of the acetic acid in the acetic acid feed and/or in any of the acetic acid recycle streams may be combined with a purified ethanol stream to form an acetic acid-denatured ethanol composition.

Other components, such as, for example, esters, ethers, aldehydes, ketones, alkanes, and carbon dioxide, if detectable, collectively may be present in amounts less than 10 wt. %, e.g., less than 6 wt. %, or less than 4 wt. %. In terms of ranges, the crude ethanol composition may comprise the other components in an amount from 0.1 wt. % to 10 wt. %, e.g., from 0.1 wt. % to 6 wt. %, or from 0.1 wt. % to 4 wt. %. Exemplary embodiments of crude ethanol compositional ranges are provided in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 10 to 60 | 15 to 50 | 25 to 50 |
| Acetic Acid | 0 to 90 | 5 to 80 | 15 to 70 | 20 to 70 |
| Water | 5 to 35 | 5 to 30 | 10 to 30 | 10 to 26 |
| Ethyl Acetate | 0 to 20 | 0 to 15 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

Figure 1B:
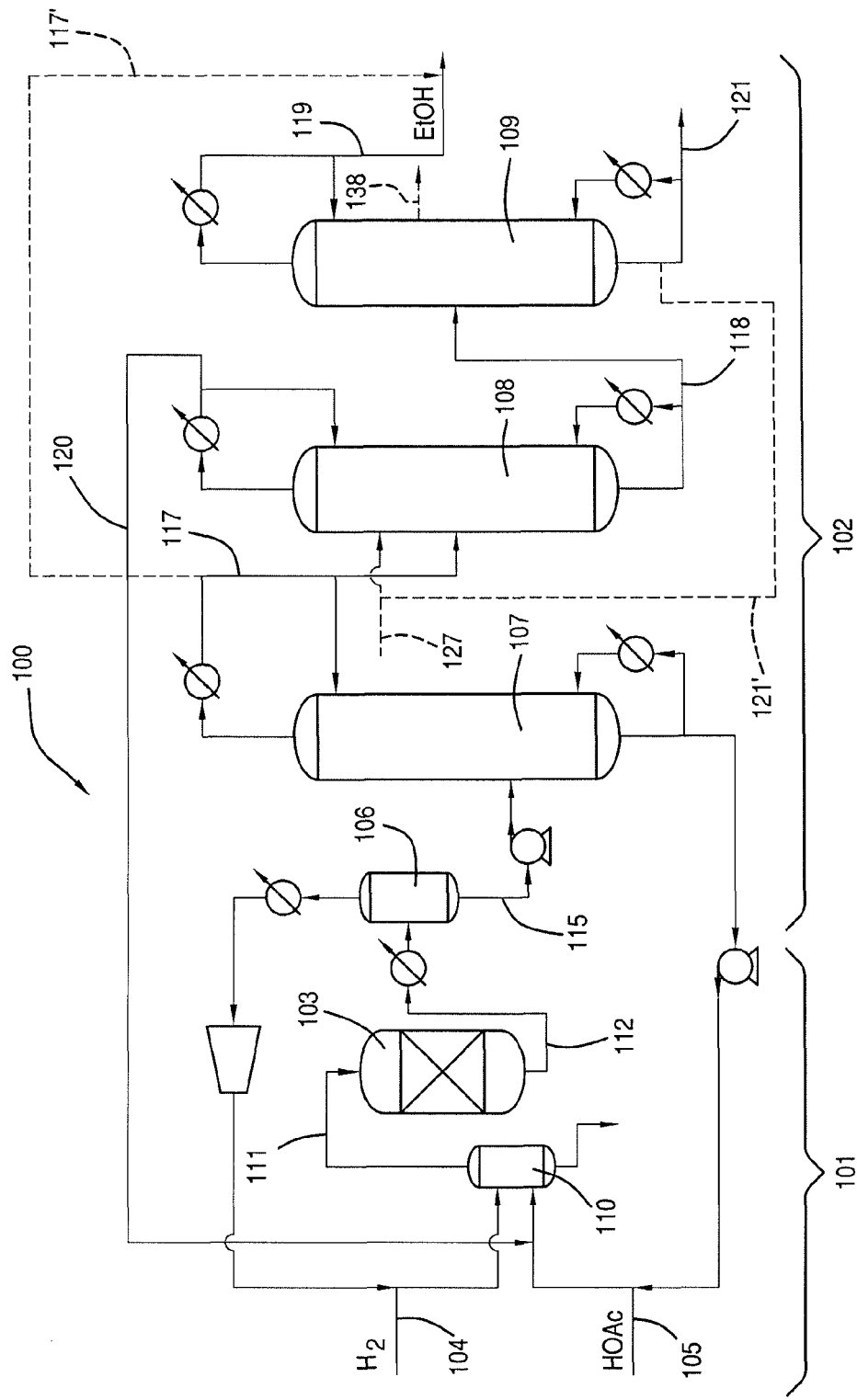
FIG. 1B is a schematic diagram of the system shown in FIG. 1A with a return of the distillate of a second column to the reactor zone.
Figure 1C:
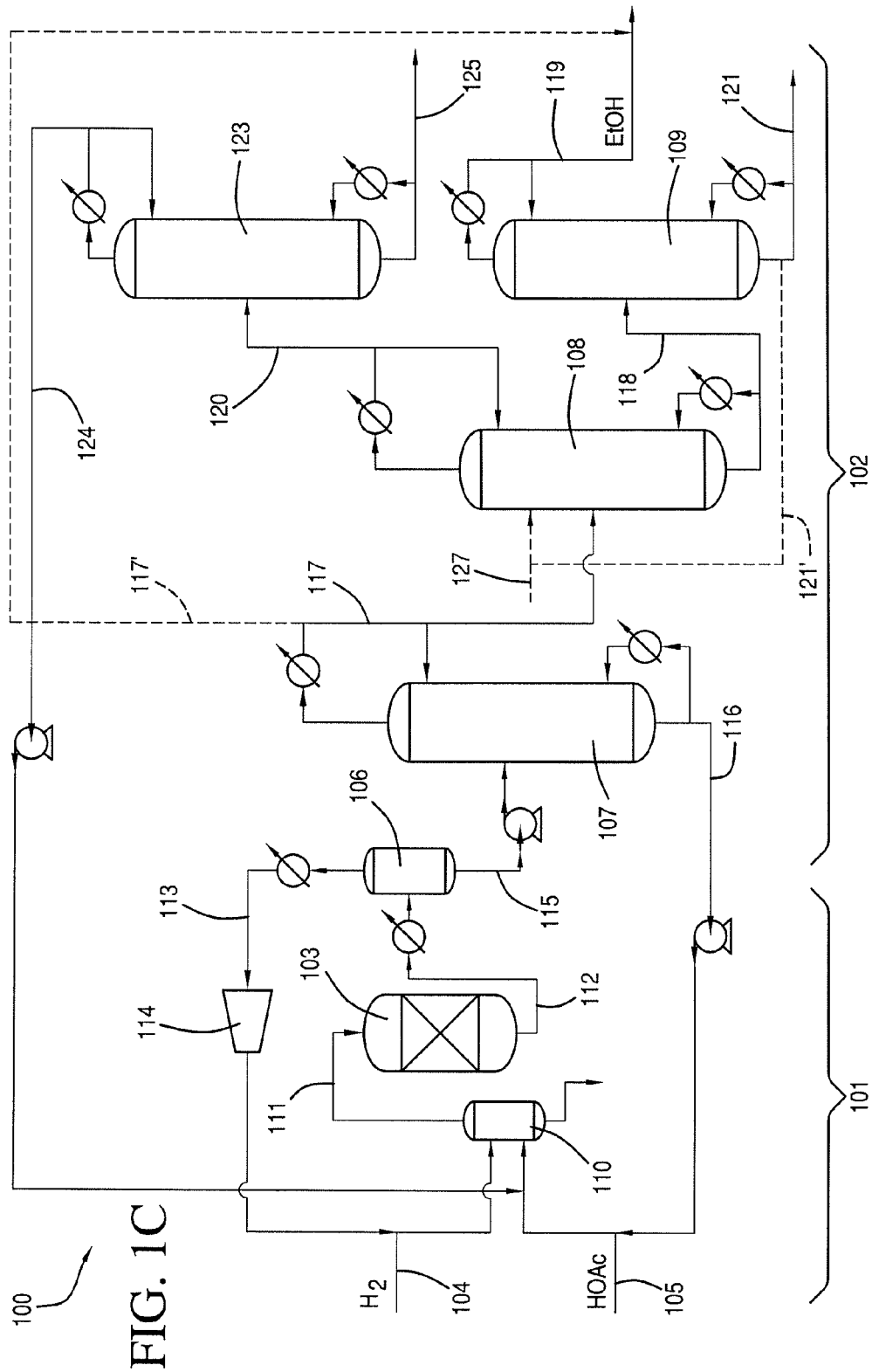
FIG. 1C is a schematic diagram of a hydrogenation system in accordance with one embodiment of the present invention.

As shown in Table 1, in some embodiments the crude ethanol product may be a denatured ethanol composition. For example, the crude ethanol composition may comprise ethanol and at least one denaturant such as acetic acid, ethyl acetate, or acetaldehyde. In other embodiments, the crude ethanol composition may be a denatured ethanol composition comprising at least one of the denaturants discussed above.
Purification FIG. 1A shows a hydrogenation system 100 suitable for the hydrogenation of acetic acid and separating ethanol from the crude reaction mixture according to one embodiment of the invention. System 100 comprises reaction zone 101 and distillation zone 102. Reaction zone 101 comprises reactor 103, hydrogen feed line 104 and acetic acid feed line 105. In other embodiments, where acetone utilized as a reactant, reaction zone 101 further comprises an acetone feed line (not shown). In other embodiments, where propionic acid utilized as a reactant, reaction zone 101 further comprises a propionic acid feed line (not shown). Distillation zone 102 comprises flasher 106, first column 107, second column 108, and third column 109. Hydrogen, acetic acid, and optionally acetone and/or propionic acid are fed to a vaporizer 110 via lines 104 and 105, respectively, to create a vapor feed stream in line 111 that is directed to reactor 103. In one embodiment, lines 104 and 105 may be combined and jointly fed to the vaporizer 110, e.g., in one stream containing both hydrogen and acetic acid. The temperature of the vapor feed stream in line 111 is preferably from 100° C. to 350° C., e.g., from 120° C. to 310° C. or from 150° C. to 300° C. Any feed that is not vaporized is removed from vaporizer 110, as shown in FIG. 1A, and may be recycled thereto. In addition, although FIG. 1A shows line 111 being directed to the top of reactor 103, line 111 may be directed to the side, upper portion, or bottom of reactor 103. Although one reactor and one flasher are shown in FIGS. 1A, 1B and 1C, additional reactors and/or components may be included in various optional embodiments of the present invention. For example, the hydrogenation system may optionally comprise dual reactors, dual flashers, heat exchanger(s), and/or pre-heater(s).

Reactor 103 contains the catalyst that is used in the hydrogenation of the carboxylic acid, preferably acetic acid. In some embodiment where acetone is a reactant and isopropanol is a desired co-product with ethanol, the catalyst in reactor 103 is selected such that, in addition to ethanol, isopropanol is also produced. As an example, a catalyst composition comprising a support such as $TiO_2$, $ZrO_2$, $Fe_2O_3$, or $CeO_2$ may be used. In some embodiments, these catalysts promote higher acetone formation. Other exemplary catalyst compositions include ruthenium supported by $SiO_2$, iron supported by carbon, or palladium supported by carbon. In other embodiments, the temperature of reactor 103 may be adjusted to achieve a desired isopropanol concentration. For example, maintaining the reaction temperature in a range of 200° C. to 350° C., e.g., from 225° C. to 300° C., may lead to an ethanol composition comprising from 0.1 wt. % to 10 wt. % isopropanol, e.g., from 1 wt. % to 9 wt. % or from 3 wt. % to 7 wt. %. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In one aspect, the guard bed media is functionalized to trap particular species such as sulfur or halogens. During the hydrogenation process, a crude ethanol product stream is withdrawn, preferably continuously, from reactor 103 via line 112. The crude ethanol product stream may be condensed and fed to flasher 106, which, in turn, provides a vapor stream and a liquid stream. The flasher 106 in one embodiment preferably operates at a temperature of from 50° C. to 500° C., e.g., from 70° C. to 400° C. or from 100° C. to 350° C. In one embodiment, the pressure of flasher 106 preferably is from 50 KPa to 2000 KPa, e.g., from 75 KPa to 1500 KPa or from 100 to 1000 KPa. In one preferred embodiment, the temperature and pressure of flasher 106 is similar to the temperature and pressure of reactor 103.

The vapor stream exiting the flasher 106 may comprise hydrogen and hydrocarbons, which may be purged and/or returned to reaction zone 101 via line 113. As shown in FIG. 1A, the returned portion of the vapor stream passes through compressor 114 and is combined with the hydrogen feed and co-fed to vaporizer 110.

The liquid from flasher 106 is withdrawn and pumped as a feed composition via line 115 to the side of first column 107, also referred to as the acid separation column. The contents of line 115 typically will be substantially similar to the product obtained directly from the reactor, and may, in fact, also be characterized as a crude ethanol product. However, the feed composition in line 115 preferably has substantially no hydrogen, carbon dioxide, methane or ethane, which are removed by flasher 106. Exemplary components of liquid in line 115 are provided in Table 2. It should be understood that liquid line 115 may contain other components, not listed, such as components in the feed.

TABLE 2

FEED COMPOSITION

| | Conc. (wt. %) | Conc. (wt. %) | Conc. (wt. %) |
|---|---|---|---|
| Ethanol | 5 to 70 | 10 to 60 | 15 to 50 |
| Water | 5 to 35 | 5 to 30 | 10 to 30 |
| Acetic Acid (Denaturant) | <90 | 5 to 80 | 15 to 70 |
| Ethyl Acetate (Denaturant) | <20 | 0.001 to 15 | 1 to 12 |
| Acetaldehyde (Denaturant) | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the feed composition, e.g., line 115, may advantageously comprise propanol, e.g., isopropanol and/or n-propanol, in small amounts, e.g., from 0.001 wt. % to 0.1 wt. %, from 0.001 wt. % to 0.05 wt. %, or from 0.001 wt. % to 0.03 wt. %. As a result of the low concentration of these alcohols, the resultant denatured ethanol composition advantageously comprises the alcohols, if at all, only in trace amounts (see discussion below). These trace amounts are significantly lower than those levels obtained via methods that do not utilize the hydrogenantion of acetic acid. In other embodiments, the concentration of isopropanol in the feed composition is higher, e.g., from 0.01 to 10 wt. %. In other embodiments, the concentration of n-propanol in the feed composition is higher, e.g., from 0.01 to 10 wt. %. In other embodiments, the concentration of diethyl ether in the feed composition is higher, e.g., from 0.01 to 20 wt. %. It should be understood that these other components may be carried through in any of the distillate or residue streams described herein. Further, as indicated above, some of these other components, e.g., isopropanol or diethyl ether, may also be utilized as denaturants.

When the content of acetic acid in line 115 is less than 5 wt. %, the acid separation column 107 may be skipped and line 115 may be introduced directly to second column 108, also referred to herein as a light ends column.

In the embodiment shown in FIG. 1A, line 115 is introduced in the lower part of first column 107, e.g., lower half or lower third. In first column 107, unreacted acetic acid, a portion of the water, and other heavy components, if present, are removed from the composition in line 115 and are withdrawn, preferably continuously, as residue. Some or all of the residue may be returned and/or recycled back to reaction zone 101 via line 116. First column 107 also forms an overhead distillate, which is withdrawn in line 117, and which may be condensed and refluxed, for example, at a ratio of from 10:1 to 1:10, e.g., from 3:1 to 1:3 or from 1:2 to 2:1.

Any of columns 107, 108 or 109 may comprise any distillation column capable of separation and/or purification. The columns preferably comprise tray columns having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in FIGS. 1A, 1B, and 1C. As shown in FIGS. 1A, 1B, and 1C, heat may be supplied to the base of each column or to a circulating bottom stream through a heat exchanger or reboiler. Other types of reboilers, such as internal reboilers, may also be used in some embodiments. The heat that is provided to reboilers may be derived from any heat generated during the process that is integrated with the reboilers or from an external source such as another heat generating chemical process or a boiler. Although one reactor and one flasher are shown in FIGS. 1A, 1B, and 1C, additional reactors, flashers, condensers, heating elements, and other components may be used in embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in any of the columns may vary. As a practical matter, pressures from 10 KPa to 3000 KPa will generally be employed in these zones although in some embodiments subatmospheric pressures may be employed as well as superatmospheric pressures. Temperatures within the various zones will normally range between the boiling points of the composition removed as the distillate and the composition removed as the residue. It will be recognized by those skilled in the art that the temperature at a given location in an operating distillation column is dependant on the composition of the material at that location and the pressure of column. In addition, feed rates may vary depending on the size of the production process and, if described, may be generically referred to in terms of feed weight ratios.

When column 107 is operated under standard atmospheric pressure, the temperature of the residue exiting in line 116 from column 107 preferably is from 95° C. to 120° C., e.g., from 105° C. to 117° C. or from 110° C. to 115° C. The temperature of the distillate exiting in line 117 from column 107 preferably is from 70° C. to 110° C., e.g., from 75° C. to 95° C. or from 80° C. to 90° C. In other embodiments, the pressure of first column 107 may range from 0.1 KPa to 510 KPa, e.g., from 1 KPa to 475 KPa or from 1 KPa to 375 KPa. Exemplary components of the distillate and residue compositions for first column 107 are provided in Table 3 below. It should also be understood that the distillate and residue may also contain other components, not listed, such as components in the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

FIRST COLUMN

| | Conc. (wt. %) | Conc. (wt. %) | Conc. (wt. %) |
|---|---|---|---|
| Distillate | | | |
| Ethanol | 20 to 75 | 30 to 70 | 40 to 65 |
| Water | 10 to 40 | 15 to 35 | 20 to 35 |
| Acetic Acid | <2 | 0.001 to 0.5 | 0.01 to 0.2 |
| Ethyl Acetate (Denaturant) | <60 | 5.0 to 40 | 10 to 30 |
| Acetaldehyde (Denaturant) | <10 | 0.001 to 5 | 0.01 to 4 |
| Isopropanol (Denaturant) | 0.02 to 7.5 | 0.3 to 6.5 | 1.2 to 5 |
| n-propanol (Denaturant | 0.02 to 7.5 | 0.3 to 6.5 | 1.2 to 5 |
| Diethyl Ether (Denaturant) | 0.02 to 7.5 | 0.3 to 6.5 | 1.2 to 5 |
| Acetal | <0.1 | <0.1 | <0.05 |
| Acetone | <0.05 | 0.001 to 0.03 | 0.01 to 0.025 |
| Residue | | | |
| Acetic Acid | 60 to 100 | 70 to 95 | 85 to 92 |
| Water | <30 | 1 to 20 | 1 to 15 |
| Ethanol | <1 | <0.9 | <0.07 |

As shown in Table 3, without being bound by theory, it has surprisingly and unexpectedly been discovered that when any amount of acetal is detected in the feed that is introduced to the acid separation column (first column 107), the acetal appears to decompose in the column such that less or even no detectable amounts are present in the distillate and/or residue.

Depending on the reaction conditions, the crude ethanol product exiting reactor 103 in line 112 may comprise ethanol, acetic acid (unconverted), ethyl acetate, and water. After exiting reactor 103, a non-catalyzed equilibrium reaction may occur between the components contained in the crude ethanol product until it is added to flasher 106 and/or first column 107. This equilibrium reaction tends to drive the crude ethanol product to an equilibrium between ethanol/acetic acid and ethyl acetate/water, as shown below.

In the event the crude ethanol product is temporarily stored, e.g., in a holding tank, prior to being directed to distillation zone 102, extended residence times may be encountered. Generally, the longer the residence time between reaction zone 101 and distillation zone 102, the greater the formation of ethyl acetate. For example, when the residence time between reaction zone 101 and distillation zone 102 is greater than 5 days, significantly more ethyl acetate may form at the expense of ethanol. Thus, shorter residence times between reaction zone 101 and distillation zone 102 are generally preferred in order to maximize the amount of ethanol formed. In one embodiment, a holding tank (not shown), is included between the reaction zone 101 and distillation zone 102 for temporarily storing the liquid component from line 115 for up to 5 days, e.g., up to 1 day, or up to 1 hour. In a preferred embodiment no tank is included and the condensed liquids are fed directly to the first distillation column 107. In addition, the rate at which the non-catalyzed reaction occurs may increase as the temperature of the crude ethanol product, e.g., in line 115, increases. These reaction rates may be particularly problematic at temperatures exceeding 30° C., e.g., exceeding 40° C. or exceeding 50° C. Thus, in one embodiment, the temperature of liquid components in line 115 or in the optional holding tank is maintained at a temperature less than 40° C., e.g., less than 30° C. or less than 20° C. One or more cooling devices may be used to reduce the temperature of the liquid in line 115.

As discussed above, a holding tank (not shown) may be included between the reaction zone 101 and distillation zone 102 for temporarily storing the liquid component from line 115, for example from 1 to 24 hours, optionally at a temperature of about 21° C., and corresponding to an ethyl acetate formation of from 0.01 wt. % to 1.0 wt. % respectively. In addition, the rate at which the non-catalyzed reaction occurs may increase as the temperature of the crude ethanol product is increased. For example, as the temperature of the crude ethanol product in line 115 increases from 4° C. to 21° C., the rate of ethyl acetate formation may increase from about 0.01 wt. % per hour to about 0.005 wt. % per hour. Thus, in one embodiment, the temperature of liquid components in line 115 or in the optional holding tank is maintained at a temperature less than 21° C., e.g., less than 4° C. or less than −10° C.

In addition, it has now been discovered that the above-described equilibrium reaction may also favor ethanol formation in the top region of first column 107.

The distillate, e.g., overhead stream, of first column 107 optionally is condensed and refluxed as shown in FIGS. 1A-C, preferably, at a reflux ratio of 1:5 to 10:1. The distillate in line 117 preferably comprises ethanol; in situ denaturant, e.g., ethyl acetate and/or acetaldehyde; water, and other impurities, which may be difficult to separate due to the formation of binary and tertiary azeotropes. The first distillate also comprises a significantly reduced amount of acetic acid. As shown in FIG. 1C, in some embodiments, the distillate of the first column (without further processing) is a denatured ethanol composition comprising from 0.0001 wt. % to 80 wt. % denaturant, e.g., from 0.001 wt. % to 60 wt. %, and from 20 wt. % to 75 wt. % ethanol, e.g., from 30 wt. % to 70 wt. %. Preferably, the denaturant in these embodiments is ethyl acetate. In other embodiments the distillate of the first column (without further processing) is a denatured ethanol composition comprising from 0.0001 wt. % to 10 wt. % denaturant, e.g., from 0.001 wt. % to 5 wt. % or from 0.01 wt. % to 4 wt. %, and from 20 wt. % to 75 wt % ethanol, e.g., from 30 wt. % to 70 wt. %. Preferably, the denaturant in these embodiments is acetaldehyde.

In another embodiment, at least a portion of the first distillate may be combined, via optional line 117', with a purified ethanol stream to form a denatured ethanol composition. Preferably, the denaturant comprises ethyl acetate and/or acetaldehyde. In another embodiment, at least a portion of the first distillate may be fed to an additional column, e.g., a third column as discussed below. As a result, the denaturant(s) in the first distillate, e.g., ethyl acetate and/or acetaldehyde, may be carried through to the distillate of the third column. As such, the third distillate may be denatured ethanol composition comprising the denaturant(s) from the first distillate. In these embodiments, the weight percentages of the denaturant(s) in the denatured ethanol composition may be as previously discussed. The weight ratio of the denaturant-containing stream, e.g., line 117, and the purified ethanol stream vary widely and may be adjusted so as to achieve a particular desired concentration of denaturant in the denatured ethanol composition. For example, the weight ratio of the purified ethanol stream to the denaturant-containing stream may range from 0.01:1 to 5:1, e.g., from 0.05:1 to 3:1.

As discussed above, the residue from first column 107 comprises an amount of unreacted acetic acid. Thus, in another embodiment, at least a portion of the first residue may be combined with a purified ethanol stream to form an acetic acid-denatured ethanol composition.

Beneficially, these denatured ethanol compositions are produced utilizing denaturant that is formed in situ via the hydrogenation reaction and without additional separation steps. As such, it is not necessary to provide an additional outside source of denaturant or to combine denaturant and purified ethanol, which eliminates a process step, and simplifies the overall process. It is also within the scope of the invention to further purify the first column distillate to remove, for example, additional water and/or acetaldehyde. Conventional separation methods may be used to achieve this additional purification.

As shown in Table 3, the first residue comprises a significant portion of unreacted acetic acid, which may, in turn, be recycled back to reactor 103, as shown in FIGS. 1A, 1B, and 1C.

The first distillate in line 117 is introduced to the second column 108, also referred to as the "light ends column," preferably in the middle part of column 108, e.g., middle half or middle third. Second column 108 may be a tray column or packed column. In one embodiment, second column 108 is a tray column having from 5 to 70 trays, e.g., from 15 to 50 trays or from 20 to 45 trays.

As one example, when a 25 tray column is utilized in a column without water extraction, line 117 is introduced at tray 17. When the second column is not an extractive distillation column, it is expected that the ethyl acetate in line 117 may be separated into the second residue along with the ethanol and water. As a result, in one embodiment, more ethyl acetate may be fed to third column 109 and, thus, this ethyl acetate may be present in the third distillate. In other embodiments, at least a portion of the ethyl acetate-containing second residue may be combined with a purified ethanol stream to form a denatured ethanol composition.

In preferred embodiments, however, the second column 108 may be an extractive distillation column. In extractive distillation columns, it is expected that the ethyl acetate in line 117 may be separated from the ethanol and water and pass into the second distillate. In such embodiments, an extraction agent, such as water, may be optionally added to second column 108 via line 127. If the extraction agent comprises water, it may be obtained from an external source or from an internal return/recycle line from one or more of the other columns. In a preferred embodiment, the water in the third residue of third column 109 is utilized as the extraction agent.

As shown in FIGS. 1A, 1B, and 1C, the third residue may be optionally directed to second column 108 via line 121'.

Although the temperature and pressure of second column 108 may vary, when at atmospheric pressure the temperature of the second residue exiting in line 118 from second column 108 preferably is from 60° C. to 90° C., e.g., from 70° C. to 90° C. or from 80° C. to 90° C. The temperature of the second distillate exiting in line 120 from second column 108 preferably is from 50° C. to 90° C., e.g., from 60° C. to 80° C. or from 60° C. to 70° C. Column 108 may operate at atmospheric pressure. In other embodiments, the pressure of second column 108 may range from 0.1 KPa to 510 KPa, e.g., from 1 KPa to 475 KPa or from 1 KPa to 375 KPa. Exemplary components for the distillate and residue compositions for second column 108 are provided in Table 4 below. It should be understood that the distillate and residue may also contain other components, not listed, such as components in the feed.

TABLE 4

SECOND COLUMN

|  | Conc. (wt. %) | Conc. (wt. %) | Conc. (wt. %) |
|---|---|---|---|
| Distillate |  |  |  |
| Ethyl Acetate (Denaturant) | 10 to 90 | 25 to 90 | 50 to 90 |
| Acetaldehyde (Denaturant) | 1 to 25 | 1 to 15 | 1 to 8 |
| Water | 1 to 25 | 1 to 20 | 4 to 16 |
| Ethanol | <30 | 0.001 to 15 | 0.01 to 5 |
| Acetal | <5 | 0.001 to 2 | 0.01 to 1 |
| Residue |  |  |  |
| Water | 30 to 70 | 30 to 60 | 30 to 50 |
| Ethanol | 20 to 75 | 30 to 70 | 40 to 70 |
| Ethyl Acetate | <3 | 0.001 to 2 | 0.001 to 0.5 |
| Acetic Acid | <0.5 | 0.001 to 0.3 | 0.001 to 0.2 |
| Isopropanol (Denaturant) | 0.01 to 10 | 0.25 to 8 | 1.5 to 6.3 |

The weight ratio of ethanol in the second residue to ethanol in the second distillate preferably is at least 3:1, e.g., at least 6:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent as the second column 108, the weight ratio of ethyl acetate in the second residue to ethyl acetate in the second distillate approaches zero. Thus, as shown in Table 4, the second distillate in line 120, which is a derivative stream of the crude ethanol product, comprises a significant amount of separated, in situ, denaturant and the second residue in line 118 comprises a significant amount of ethanol. In some embodiments, the second distillate comprises diethyl ether. The diethyl ether may be present in amounts ranging from 0.1 wt. % to 20 wt. %, e.g., 0.1 wt. % to 10 wt. %, from 1 wt. % to 9 wt. %, or from 3 wt. % to 7 wt. %. In these cases, the second distillate may be a denatured ethanol composition having a diethyl ether denaturant. In one embodiment, the second residue in line 118 further comprises isopropanol. The isopropanol may be derived from acetone via the methods discussed above. The acetone, for example, may be formed in situ in the hydrogenation and/or the acetone may be added to the hydrogenation reactor as a reactant. Thus, in embodiments where a sufficient amount of isopropanol, e.g., from 0.1 wt. % to 10 wt. %, from 1 wt. % to 9 wt. %, or from 3 wt. % to 7 wt. %, is present in the second residue, the second residue may be a denatured ethanol composition having an isopropanol denaturant.

In another embodiment of the invention as shown in FIG. 1A, at least a portion of the second distillate is directed, e.g., via line 120, to the purified ethanol exiting third column 109. In this case, the denatured ethanol composition results from the addition of the in situ-formed denaturant to the purified ethanol. Preferably, ethyl acetate denaturant in the second distillate is combined with the purified ethanol obtained from third column 109. In other embodiments, acetaldehyde denaturant in the second distillate is combined with the purified ethanol obtained from third column 109. In other embodiments, at least a portion of the second distillate is fed to third column 109. In these cases, at least a portion of the denaturant in the second distillate, e.g., ethyl acetate and/or acetaldehyde, follows the ethanol through third column 109. Other impurities in the second distillate may be withdrawn in the residue of the third column 109. As a result, the third distillate comprises ethanol along with denaturant from the second column distillate. Denatured ethanol compositions thus formed may have the characteristics and composition of the denatured ethanol compositions discussed herein. The weight ratio of the denaturant-containing stream, e.g., line 120, and the purified ethanol stream vary widely and may be adjusted so as to achieve a particular desired concentration of denaturant in the denatured ethanol composition. For example, when ethyl acetate is the denaturant, the weight ratio of the purified ethanol stream to the denaturant-containing stream may range from 100:1 to 1:1, e.g., from 25:1 to 5:1.

In another embodiment, at least a portion of the second distillate is recycled to reactor 103 (not shown). As shown, the second residue from the bottom of second column 108, which comprises ethanol and water, is fed via line 118 to third column 109, also referred to as the "product column." More preferably, the second residue in line 118 is introduced in the lower part of third column 109, e.g., lower half or lower third. Third column 109 recovers ethanol, which preferably is substantially pure other than the azeotropic water content, as the distillate in line 119. The distillate of third column 109 preferably is refluxed as shown in FIG. 1A, for example, at a reflux ratio of from 1:10 to 10:1, e.g., from 1:3 to 3:1 or from 1:2 to 2:1. The third residue in line 121, which preferably comprises primarily water, preferably is removed from the system 100 or may be partially returned to any portion of the system 100. Third column 109 is preferably a tray column as described above and preferably operates at atmospheric pressure. The temperature of the third distillate exiting in line 119 from third column 109 preferably is from 60° C. to 110° C., e.g., from 70° C. to 100° C. or from 75° C. to 95° C. The temperature of the third residue exiting from third column 109 preferably is from 70° C. to 115° C., e.g., from 80° C. to 110° C. or from 85° C. to 105° C., when the column is operated at atmospheric pressure. Exemplary components of the distillate, residue, and optional side stream compositions for third column 109 are provided in Table 5 below. As shown in Table 5, the third distillate may comprise significant amounts of isopropanol denaturant. In these cases, the third distillate may be a denatured ethanol composition. It should be understood that the distillate and residue may also contain other components, not listed, such as components in the feed.

As separation occurs in the third column, the composition of the stream being separated may vary from tray to tray in the third column. In some embodiments, the composition of the stream within the third column, depending upon operating conditions, may contain an increased concentration or build up of alcohols, e.g., mid-boiling alcohols having a boiling point lower than that of water and higher than that of an ethanol/water low-boiling azeotrope. Examples of these alcohols include n-propanol (boiling point 97.1° C.), isopropanol (boiling point 82.5° C.), and 2-butanol (boiling point 99.5° C.). Some of these alcohols were formed in situ as a result of the acetic acid hydrogenation. Preferably, these in situ-formed mid-boiling alcohols may be utilized as denaturants.

The mid-boiling point alcohols may be removed using one or more side streams 138 drawn from third column 109. Preferably, side stream 138 is drawn from a middle or an upper section of third column 109, above the feed point of the second residue. Most preferably, side stream 138 is drawn from above the tray 25, e.g., from above tray 30, or from above tray 40. By adjusting the process parameters of third column 109 and withdrawing side stream 138 at the appropriate location, side stream 138 beneficially removes a significant portion of mid-boiling point alcohols, e.g., n-propanol, from the feed in line 118. Side stream 138 preferably comprises from 0.01 wt. % to 10 wt. % n-propanol, e.g., from 0.01 to 5 wt. % or from 0.01 wt. % to 3 wt. %. By withdrawing side stream 138, a significant amount of n-propanol is removed resulting in the purification of the ethanol in the third distillate in line 119. It is within the scope of the invention to select, based on column configuration and operating conditions, an appropriate tray in a column from which to draw a particular side stream. Also, the contents of side stream 138 may constitute a denatured ethanol composition comprising ethanol and n-propanol. Thus, in this embodiment, a pure ethanol composition may be co-produced with a denatured ethanol composition. In other embodiments, side stream 138 and third distillate are each, independently of one another, denatured ethanol compositions. For example, side stream 130 may comprise an n-propanol-denatured ethanol composition and third distillate 119 may comprise an ethyl acetate-denatured ethanol composition. By performing the separation in this manner, the resultant third distillate 119 beneficially comprises less n-propanol. In other embodiments, at least a portion of withdrawn side stream 138 may be combined with third distillate 119 to form a denatured ethanol composition comprising at least a portion of the in situ-formed denaturant from side stream 130.

TABLE 5

THIRD COLUMN

|  | Conc. (wt. %) | Conc. (wt. %) | Conc. (wt. %) |
|---|---|---|---|
| Distillate |  |  |  |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Isopropanol | 0.07 to 10 | 0.8 to 7 | 2.5 to 7 |
| Residue |  |  |  |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |
| Side Stream (Optional) |  |  |  |
| Ethanol | 0.01 to 10 | 0.01 to 5 | 0.01 to 3 |
| n-propanol | 0.1 to 10 | 0.25 to 8 | 1.5 to 6.3 |

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns 107, 108, and/or 109 in system 100. In one embodiment, at least one side stream may be used to remove impurities from the third column 109. The impurities may be purged and/or retained within the system 100.

The third distillate in line 119 may be further purified to form an anhydrous ethanol product stream, i.e., "finished anhydrous ethanol," using one or more additional separation systems, such as, for example, distillation columns (e.g., a finishing column) or molecular sieves.

Returning to second column 108, the distillate in line 120 preferably is refluxed as shown in FIGS. 1A, 1B, and 1C, for example, at a reflux ratio of from 1:10 to 10:1, e.g., from 1:5 to 5:1 or from 1:3 to 3:1. As noted above, the second distillate comprises a significant portion of denaturant, e.g., ethyl acetate and/or acetaldehyde. Accordingly, all or a portion of the second distillate, as shown by line 120, may be directed downstream and may be combined with ethanol that has been further purified, e.g., via third column 109. Also, at least a portion of the distillate from second column 108 may be purged if necessary. In another embodiment, as shown in FIG. 1B, a portion of the second distillate from second column 108 may be recycled to reaction zone 101 via line 120 in order to convert ethyl acetate to additional ethanol, e.g., may be recycled to reactor 103 and co-fed along with acetic acid feed line 105. In another embodiment, the second distillate in line 120 may be further purified to remove other components, such as acetaldehyde, using one or more additional columns (not shown). Such a configuration may be utilized in a case where the desired denaturant consists essentially of ethyl acetate, e.g., Formulae 35 or 35-A of Title 27, Part 21 of the US Code of Federal Regulations (hereinafter abbreviated as 27 C.F.R. Part 21), the entirety of which is incorporated herein by reference. As another option, additional columns (not shown) may be utilized to remove the ethyl acetate and leave acetaldehyde, which may be useful in a situation where the desired denaturant comprises acetaldehyde and does not comprise ethyl acetate.

System 100 in FIG. 1C is similar to that of FIGS. 1A and 1B, with the addition that the second distillate in line 120 is fed to fourth column 123, also referred to as the "acetaldehyde removal column." In fourth column 123, the second distillate is separated into a fourth distillate, which comprises acetaldehyde in line 124 and a fourth residue, which comprises ethyl acetate in line 125. The fourth distillate preferably is refluxed at a reflux ratio of from 1:20 to 20:1, e.g., from 1:10 to 10:1 or from 1:5 to 5:1, and at least a portion of the fourth distillate may be returned to the reaction zone 101 as shown by line 124. For example, the fourth distillate may be combined with the acetic acid feed, added to the vaporizer 110, or added directly to the reactor 103. As shown, the fourth distillate is co-fed with the acetic acid in feed line 105 to vaporizer 110. Without being bound by theory, since acetaldehyde may be hydrogenated to form ethanol, the recycling of a stream that contains acetaldehyde to the reaction zone increases the yield of ethanol and decreases byproduct and waste generation. In another embodiment (not shown in the figure), the acetaldehyde may be collected and utilized, with or without further purification, to make useful products including but not limited to n-butanol, 1,3-butanediol, and/or crotonaldehyde and derivatives. In one preferred embodiment, the acetaldehyde is removed from the second distillate in fourth column 123 such that no detectable amount of acetaldehyde is present in the residue of column 123.

In preferred embodiments, at least a portion of fourth distillate is combined (not shown) with a purified ethanol stream to form a denatured ethanol composition. Preferably, the denaturant comprises acetaldehyde and/or ethyl acetate. In other embodiments, at least a portion of the fourth distillate may be fed to third column 109. As a result, in these embodiments, the distillate exiting third column 109 may comprise at least a portion of the in situ-formed acetaldehyde and/or ethyl acetate that was present in the fourth distillate. In these embodiments, the weight percentages of the acetaldehyde denaturant in the denatured ethanol composition may be as previously discussed. The weight ratio of the purified ethanol stream and the fourth distillate may vary widely and may be adjusted so as to achieve a particular desired concentration of denaturant in the denatured ethanol composition. For example, the weight ratio of the purified ethanol stream to the fourth distillate may range from 2:1 to 75:1, e.g., from 7:1 to 50:1.

The fourth residue primarily comprises ethyl acetate and ethanol. Preferably, at least a portion of fourth residue is combined with a purified ethanol stream to form a denatured ethanol composition. Preferably, the denaturant comprises ethyl acetate. In other embodiments, at least a portion of the fourth residue may be fed to third column 109. As a result, in these embodiments, the distillate exiting third column 109 may comprise at least a portion of the in situ-formed ethyl acetate that was present in the fourth residue. In these embodiments, the weight percentages of the ethyl acetate denaturant in the denatured ethanol composition may be as previously discussed. The weight ratio of the purified ethanol stream and the fourth residue may vary widely and may be adjusted so as to achieve a particular desired concentration of denaturant in the denatured ethanol composition. For example, the weight ratio of the purified ethanol stream to the fourth residue may range from 1:1 to 50:1, e.g., from 1.75:1 to 20:1. The fourth residue of fourth column 123, in other embodiments, may be purged via line 125.

Fourth column 123 is preferably a tray column as described above and preferably operates above atmospheric pressure. In one embodiment, the pressure is from 120 KPa to 5,000 KPa, e.g., from 200 KPa to 4,500 KPa, or from 400 KPa to 3,000 KPa. In a preferred embodiment the fourth column 123 may operate at a pressure that is higher than the pressure of the other columns.

The temperature of the fourth distillate exiting in line 124 from fourth column 123 preferably is from 60° C. to 110° C., e.g., from 70° C. to 100° C. or from 75° C. to 95° C. The temperature of the residue exiting from fourth column 125 preferably is from 70° C. to 115° C., e.g., from 80° C. to 110° C. or from 85° C. to 110° C. Exemplary components of the distillate and residue compositions for fourth column 123 are provided in Table 6 below. It should be understood that the distillate and residue may also contain other components, not listed, such as components in the feed.

TABLE 6

FOURTH COLUMN

| | Conc. (wt. %) | Conc. (wt. %) | Conc. (wt. %) |
|---|---|---|---|
| Distillate | | | |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue | | | |
| Ethyl Acetate | 40 to 100 | 50 to 100 | 60 to 100 |
| Ethanol | <40 | 0.001 to 30 | 0 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

FIG. 1C also shows that the third residue in line 121 may be recycled to second column 108. In one embodiment, recycling the third residue further reduces the aldehyde components in the second residue and concentrates these aldehyde components in the distillate stream 120 and thereby sent to the fourth column 123, wherein the aldehydes may be more easily separated in the fourth column 123. Such embodiments also provide a finished ethanol product that preferably has low amounts of aldehydes and esters.

In several embodiments, denaturant-containing streams are combined with purified ethanol streams to form denatured ethanol compositions. In other embodiments, these denaturant-containing streams may be fed to third column 109, as opposed to being combined with the distillate of third column 109. In these cases, the denaturants that are fed to column 109 may be separated in the distillate of the third column 109 and, as such may be present in the purified ethanol. Thus, the third distillate may comprise a denatured ethanol composition.

Denatured Ethanol Compositions

As noted above, the denatured ethanol composition obtained by the processes of the present invention comprises ethanol and at least one, e.g., at least two or at least three, denaturant(s). The denaturant may be produced in situ via the hydrogenation reaction, thus eliminating the need for an outside denaturant source. Preferably, the denaturant comprises ethyl acetate, acetaldehyde, diethyl ether, acetic acid, isopropanol and/or mixtures thereof.

The denaturant, thus produced, should be present in an effective amount, e.g., in an amount sufficient to provide for a denatured ethanol composition in accordance with appropriate government regulations. As used herein, the term "denatured ethanol composition" means a composition comprising ethanol and one or more denaturants that is unfit for beverage or internal human medicine, e.g., unpalatable. In other embodiments, the denatured ethanol may comprise a "specifically denatured ethanol," which is an ethanol composition that is denatured pursuant to the formulae authorized under 27 C.F.R. Part 21, Subpart D. In addition, requirements for denatured ethanols are different for different applications, e.g., fuel applications and industrial applications. Thus, some applications may require higher amounts of denaturants while other applications may require lower amounts. A listing of some of these applications is provided in 27 C.F.R. Part 21, the entirety of which is incorporated herein by reference. Table 7 indicates some of the denatured compositions in terms of the amount of denaturant that is added to 100 gallons of ethanol.

TABLE 7

US Denatured Alcohol Formulae According to 27 C.F.R. Part 21

| Formula | Denaturant | Amount (gallons) |
|---|---|---|
| Formula 3-C | isopropyl alcohol | 5 |
| Formula 13-A | ethyl ether | 10 |
| Formula 18* | vinegar 90-grain strength (9% acetic acid in water) | 100 |
| Formula 18* | vinegar 60-grain strength (6% acetic acid in water) | 150 |
| Formula 29 | acetaldehyde | 1 |
| Formula 29 | alcohol solution containing not less than 20% acetaldehyde | 5 |
| Formula 29 | ethyl acetate | 1 |
| Formula 32 | ethyl ether | 5 |
| Formula 35 | ethyl acetate | 29.75 |
| Formula 35 | mixture of ethyl acetate with an ester content of not less than 85 percent by weight | 35 |
| Formula 35-A | ethyl acetate | 4.25 |

TABLE 7-continued

US Denatured Alcohol Formulae According to 27 C.F.R. Part 21

| Formula | Denaturant | Amount (gallons) |
|---|---|---|
| Formula 35-A | mixture of ethyl acetate with an ester content of not less than 85 percent by weight | 5 |

*Ethanol is not less than 160 proof.

In addition, in other embodiments, the inventive denatured ethanol compositions, as formed, corresponds to the denatured formulae of countries other than the United States. For example, in the United Kingdom, one formula for trade specific denatured alcohol is as follows. With every 979 parts by volume of alcohol (of a strength of not less than 85 percent alcohol by volume) mix not less than 20 parts by volume of ethyl acetate and 1 part by volume of isopropyl alcohol.

Another exemplary United Kingdom trade specific denatured alcohol formula is as follows. With every 950 parts by volume of alcohol (of a strength of not less than 85 percent alcohol by volume) mix not less than 50 parts by volume of isopropyl alcohol.

Of course, this listing of US and international denatured ethanol composition formulae is not exclusive and other formula are certainly within the scope of the invention.

Preferably, the denatured ethanol composition comprises from 50 wt. % to 99 wt. % ethanol, e.g., from 60 wt. % to 99 wt. % or from 70 wt. % to 95 wt. %, and from 0.01 wt. % o 40 wt. % denaturant, e.g., from 0.01 wt. % to 25 wt. %, from 0.01 wt. % to 20 wt. %, or from 1 wt. % to 15 wt. %, based on the total weight of the denatured ethanol composition.

In addition to the ethanol and the denaturant, the denatured ethanol composition may also comprise only trace amounts of other impurities such as acetic acid; $C_3$ alcohols, e.g., n-propanol and isopropanol; and/or $C_4$-$0_5$ alcohols.

In some embodiments, the inventive denatured ethanol composition comprises at least a portion of the first column distillate, as discussed above. Here, the denatured ethanol composition may comprise as the denaturant ethyl acetate and/or acetaldehyde. Exemplary weight percentage ranges for the ethanol and the denaturants (as well as other optional components) are provided in Table 3 above. Preferably, the amount of total denaturant (ethyl acetate and acetaldehyde) in these denatured ethanol compositions ranges from 0.01 wt. % to 90 wt. % denaturant, e.g., from 0.01 wt. % to 65 wt. % or from 0.01 wt. % to 34 wt. %.

In other embodiments, the denatured ethanol composition is withdrawn from a separation tower in the separation zone. In these cases, the ethanol composition may, for example, comprise an isopropanol denaturant in an amount ranging from 0.1 wt. % to 10 wt. % isopropanol, e.g., from 1 wt. % to 9 wt. % or from 3 wt. % to 7 wt. %.

In other embodiments, the ethanol composition comprises an ethyl ether, e.g., diethyl ether, denaturant in an amount ranging from 0.1 wt. % to 20 wt. % diethyl ether, e.g., from 0.1 wt. % to 10 wt. %, from 1 wt. % to 9 wt. % or from 3 wt. % to 7 wt. %. In other embodiments, the ethanol composition comprises an acetic acid denaturant in an amount ranging from 0.1 wt. % to 20 wt. % acetic acid, e.g., from 1 wt. % to 15 wt. % or from 2 wt. % to 12 wt. %. In other embodiments, the ethanol composition comprises an n-propanol denaturant in an amount ranging from 0.001 wt. % to 10 wt. % n-propanol, e.g., from 0.001 wt. % to 0.1 wt. %, from 0.1 wt. % to 10 wt. %, from 1 wt. % to 9 wt. %, or from 3 wt. % to 7 wt. %.

In preferred embodiments, the denatured ethanol composition is formed by combining a crude ethanol product derivative stream comprising denaturant, e.g., the second distillate, and a purified ethanol stream. Exemplary weight percentage ranges for the ethanol and the denaturants, e.g., ethyl acetate and/or acetaldehyde, (as well as other optional components) are provided in Table 8. In some embodiments, the ethanol composition comprises an ethyl acetate denaturant in an amount ranging from 0.01 wt. % to 40 wt. % ethyl acetate, e.g., from 0.01 wt. % to 15 wt. %, from 0.01 wt. % to 10 wt. % or from 0.01 wt. % to 9 wt. %. In other embodiments, the ethanol composition comprises an acetaldehyde denaturant in an amount ranging from 0.01 wt. % to 10 wt. % acetaldehyde, e.g., from 0.01 wt. % to 5 wt. %, from 0.01 wt. % to 2 wt. % or from 0.01 wt. % to 1 wt. %. Preferably, the amount of total denaturant in these denatured ethanol compositions ranges from 0.01 wt. % to 20 wt. % denaturant, e.g., from 0.01 wt. % to 12 wt. % or from 0.01 wt. % to 10 wt. %.

TABLE 8

DENATURED ETHANOL COMPOSITIONS

| Component | Conc. (wt. %) | Conc. (wt. %) | Conc. (wt. %) |
|---|---|---|---|
| Ethanol | 50 to 99 | 60 to 99 | 70 to 95 |
| Water | 0.0001 to 1 | 0.001 to 0.1 | 0.001 to 0.05 |
| Acetic Acid | 1 to 20 | 3 to 15 | 5 to 10.5 |
| Ethyl Acetate (Denaturant) | <15 | <10 | <9 |
| Acetaldehyde (Denaturant) | <10 | <5 | <3 |
| Isopropanol (Denaturant) | 0.05 to 10 | 0.6 to 9 | 2 to 6.7 |
| Diethyl Ether (Denaturant) | 0.05 to 10 | 0.6 to 9 | 2 to 6.7 |
| N-propanol (Denaturant) | 0.05 to 10 | 0.6 to 9 | 2 to 6.7 |
| Acetal | <0.05 | <0.01 | <0.005 |
| Acetone | <0.05 | <0.01 | <0.005 |

Although the exemplary weight percentages of water in the embodiments of Table 8 range from 0.0001 wt. % to 1 wt. %, in other embodiments, water may be present in the denatured ethanol composition in greater amounts. For example, the denatured ethanol composition may comprise water in an amount ranging from 0.1 wt. % to 8 wt. % water, e.g., from 0.1 wt. % to 5 wt. % or from 0.1 wt. % to 2 wt. %.

The denatured ethanol compositions of the embodiments of the present invention may be suitable for use in a variety of applications including fuels, solvents, chemical feedstocks, pharmaceutical products, cleansers, sanitizers, or hydrogenation transport. In fuel applications, the denatured ethanol composition may be blended with gasoline for motor vehicles such as automobiles, boats and small piston engine aircrafts. In non-fuel applications, the denatured ethanol composition may be used as a solvent for toiletry and cosmetic preparations, detergents, disinfectants, coatings, inks, and pharmaceuticals. The denatured ethanol composition may also be used as a processing solvent, e.g., in manufacturing processes for medicinal products, food preparations, dyes, photochemicals and latex processing.

The denatured ethanol composition may also be used as a chemical feedstock to make other chemicals such as vinegar, ethyl acrylate, ethyl acetate, ethylene, glycol ethers, ethylamines, aldehydes, and higher alcohols, especially butanol. The denatured ethanol composition may be suitable for use as a feed stock in esters production. Preferably, in the production of ethyl acetate, the denatured ethanol composition may be esterified with acetic acid or reacted with polyvinyl acetate. The denatured ethanol composition may be dehydrated to produce ethylene. Any of known dehydration catalysts can be employed to dehydrate ethanol, such as those described in copending U.S. application Ser. No. 12/221,137 and U.S. application Ser. No. 12/221,138, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated by reference.

In order that the invention disclosed herein may be more efficiently understood, some non-limiting examples are provided below. The following examples describe various embodiments of the inventive ethanol composition.

EXAMPLES

Example 1

A crude ethanol product comprising ethanol, acetic acid, water, and ethyl acetate was produced by reacting a vaporized feed comprising 95.2 wt. % acetic acid and 4.6 wt. % water with hydrogen in the presence of a catalyst comprising 1.6 wt. % platinum and 1 wt. % tin supported on ⅛ inch calcium silicate modified silica extrudates at an average temperature of 291° C., an outlet pressure of 2,063 KPa. Unreacted hydrogen was recycled back to the inlet of the reactor such that the total hydrogen/acetic acid molar ratio was 5.8 at a GHSV of 3,893 hr$^{-1}$. Under these conditions, 42.8% of the acetic acid was converted, and the selectivity to ethanol was 87.1%, selectivity to ethyl acetate was 8.4%, and selectivity to acetaldehyde was 3.5%. The crude ethanol mixture was purified using a separation scheme having distillation columns as shown in FIG. 1A.

The crude ethanol product was fed to the first column at a feed rate of 20 g/min. The composition of the liquid feed is provided in Table 8. The first column was a 2 inch diameter Oldershaw with 50 trays. The column was operated at a temperature of 115° C. at atmospheric pressure. Unless otherwise indicated, a column operating temperature is the temperature of the liquid in the reboiler and the pressure at the top of the column is atmospheric (approximately one atmosphere). The column differential pressure between the trays in the first column was 7.4 KPa. The first residue was withdrawn at a flow rate of 12.4 g/min and returned to the hydrogenation reactor.

The first distillate was condensed and refluxed at a 1:1 ratio at the top of the first column, and a portion of the distillate was introduced to the second column at a feed rate of 7.6 g/min. The second column was a 2 inch diameter Oldershaw design equipped with 25 trays. The second column was operated at a temperature of 82° C. at atmospheric pressure. In this embodiment, an extractive agent was not utilized. The column differential pressure between the trays in the second column was 2.6 KPa. The second residue was withdrawn at a flow rate of 5.8 g/min and directed to the third column. The second distillate was refluxed at a ratio of 4.5:0.5 and the remaining distillate was collected for analysis. The compositions of the feed, distillates, and residues are provided in Table 9.

TABLE 9

| Component | Feed (wt. %) | First Column Distillate (wt. %) | First Column Residue (wt. %) | Second Column Distillate (wt. %) | Second Column Residue (wt. %) |
|---|---|---|---|---|---|
| Water | 13.8 | 24.7 | 5.6 | 5.1 | 30.8 |
| Acetaldehyde | — | 1.8 | — | 8.3 | — |
| Acetic Acid | 55.0 | 0.08 | 93.8 | 0.03 | 0.1 |
| Ethanol | 23.4 | 57.6 | 0.06 | 12.4 | 67.6 |
| Ethyl Acetate | 6.5 | 15.1 | — | 76.0 | — |
| Acetal | 0.7 | 0.1 | — | 0.006 | 0.03 |
| Acetone | — | 0.01 | — | 0.03 | — |

As shown in Table 9, the first column distillate is a denatured ethanol composition, which comprises ethanol and a significant portion of in situ-formed denaturant.

Residue from the second column was collected from several runs and introduced (above tray 25) to the third column, a 2 inch Oldershaw containing 60 trays, at a rate of 10 g/min. The third column was operated at a temperature of 103° C. at atmospheric pressure. The column differential pressure between the trays in the third column was 6.2 KPa. The third residue was withdrawn at a flow rate of 2.7 g/min. The third distillate was condensed and refluxed at a 3:1 ratio at the top of the third column. The composition of the recovered ethanol composition is shown in Table 10. The ethanol composition comprises ethanol and a significant portion of in situ-formed ethyl acetate. This denatured ethanol composition was, surprisingly and unexpectedly, a denatured ethanol composition that was prepared without the addition of outside denaturant. The ethanol composition also contained 10 ppm of n-butyl acetate.

TABLE 10

| Component | Third Column Feed (wt. %) | Third Column Distillate (wt. %) | Third Column Residue (wt. %) |
|---|---|---|---|
| Acetic Acid | 0.098 | 0.001 | 0.4 |
| Ethanol | 65.7 | 93.8 | 0.004 |
| Water | 35.5 | 6.84 | 98 |
| Ethyl Acetate | 1.37 | 1.8 | — |
| Acetal | 0.02 | 0.03 | — |
| Isopropanol | 0.004 | 0.005 | — |
| n-propanol | 0.01 | 0 | — |

Example 2

A crude ethanol product comprising ethanol, acetic acid, water and ethyl acetate was produced by reacting a vaporized feed comprising 96.3 wt. % acetic acid and 4.3 wt. % water with hydrogen in the presence of a catalyst comprising 1.6 wt. % platinum and 1% tin supported on ⅛ inch calcium silicate modified silica extrudates at an average temperature of 290° C., an outlet pressure of 2,049 KPa. Unreacted hydrogen was recycled back to the inlet of the reactor such that the total hydrogen/acetic acid molar ratio was 10.2 at a GHSV of 1,997 hr$^{-1}$. Under these conditions, 74.5% of the acetic acid was converted, and the selectivity to ethanol was 87.9%, selectivity to ethyl acetate was 9.5%, and selectivity to acetaldehyde was 1.8%. The crude ethanol mixture was purified using a separation scheme having distillation columns as shown in FIG. 1A.

The crude ethanol product was fed to the first column at a feed rate of 20 g/min. The composition of the liquid feed is provided in Table 11. The first column is a 2 inch diameter Oldershaw with 50 trays. The column was operated at a temperature of 116° C. at atmospheric pressure. The column differential pressure between the trays in the first column was 8.1 KPa. The first residue was withdrawn at a flow rate of 10.7 g/min and returned to the hydrogenation reactor.

The first distillate was condensed and refluxed at a 1:1 ratio at the top of the first column, and a portion of the distillate was introduced to the second column at a feed rate of 9.2 g/min. The second column is a 2 inch diameter Oldershaw design equipped with 25 trays. The second column was operated at a temperature of 82° C. at atmospheric pressure. The column differential pressure between the trays in the second column was 2.4 KPa. The second residue was withdrawn at a flow rate of 7.1 g/min and directed to the third column. The second distillate was refluxed at a ratio of 4.5:0.5 and the remaining distillate was collected for analysis. The compositions of the feed, distillates, and residues are provided in Table 11.

TABLE 11

| | | First Column | | Second Column | |
|---|---|---|---|---|---|
| Component | Feed (wt. %) | Distillate (wt. %) | Residue (wt. %) | Distillate (wt. %) | Residue (wt. %) |
| Water | 14.6 | 27.2 | 3.7 | 3.0 | 36.2 |
| Acetaldehyde | — | 1.5 | — | 10.3 | — |
| Acetic Acid | 49.1 | 0.2 | 98.2 | 0.04 | 0.3 |
| Ethanol | 27.6 | 54.5 | 0.04 | 13.3 | 64.4 |
| Ethyl Acetate | 7.9 | 15.2 | — | 75.7 | 1.8 |
| Acetal | 0.7 | 0.1 | — | 0.01 | 0.02 |
| Acetone | — | 0.01 | — | 0.03 | — |

As shown in Table 11, the first column distillate is a denatured ethanol composition, which comprises ethanol and a significant portion of in situ-formed denaturant.

Example 3

A crude ethanol product comprising ethanol, isopropanol, acetic acid, water, and ethyl acetate was produced by reacting a vaporized feed comprising 98 wt. % acetic acid and 2 wt. % acetone with hydrogen in the presence of a catalyst comprising 1.6 wt. % platinum and 1 wt. % tin supported on ⅛ inch calcium silicate modified silica extrudates at an average temperature of 291° C., an outlet pressure of 1,420 KPa. The catalyst was diluted at a volume ratio of 1:1 with 3 mm glass beads. Under these conditions, the acetone conversion was 68% and, after separation, the resulting ethanol/isopropanol mixture comprised 4.3 wt. % isopropanol.

The composition of the resultant crude ethanol composition is provided in Table 12.

TABLE 12

| Component | wt. % |
|---|---|
| Ethanol | 30.7 |
| Acetaldehyde | 0.3 |
| Acetone | 0.6 |
| Isopropanol | 1.3 |
| Ethyl Acetate | 3.4 |
| Acetic Acid | 50.9 |
| Acetal | 0.5 |

As shown in Table 12, the addition of acetone to the acetic acid feed provides for isopropanol product when the acetic acid feed is hydrogenated. The crude ethanol product formed from the hydrogenation provides for a denatured ethanol composition comprising the ethanol and 4.3 wt. % of the in situ-formed isopropanol.

In other embodiments, the denatured ethanol composition is formed by combining a crude ethanol product derivative stream comprising denaturant and a purified ethanol stream. As such, denaturants from the derivative stream are combined with the purified ethanol stream.

Example 4

A crude ethanol product comprising ethanol, acetic acid, acetaldehyde, water, and ethyl acetate was prepared via acetic acid hydrogenation as discussed above. The crude ethanol product was purified using a separation scheme having distillation columns as shown in FIG. 1A. The second column was operated as an extractive distillation column with a water extraction agent.

The compositions of the distillate exiting the second column and the distillate exiting the third column are provided in Table 13.

TABLE 13

| Component | Second Distillate (wt. %) | Third Distillate (wt. %) |
|---|---|---|
| Ethanol | 12.4 | 93.8 |
| Ethyl Acetate | 76 | 1.8 |
| Acetaldehyde | 8.3 | 0 |
| Acetic Acid | 0.03 | 0.001 |
| Isopropanol | 0 | 0.005 |
| N-propanol | 0 | 0 |
| Acetone | 0.03 | 0 |
| Acetal | 0.006 | 0.03 |
| Water | 5.1 | 6.8 |

The second distillate and the third distillate of Table 13, when combined at a weight ratio of 1.6:1 and 21:1, respectively, provides for a denatured ethanol compositions as shown in Table 14.

TABLE 14

| Component | 1.6:1 Weight Ratio wt. % | 21:1 Weight Ratio wt. % |
|---|---|---|
| Ethanol | 61 | 88 |
| Ethyl Acetate | 30 | 5 |
| Acetaldehyde | 3 | 0.4 |
| Acetic Acid | 0.01 | 0.002 |
| Isopropanol | 0.003 | 0.005 |
| N-propanol | 0 | 0 |
| Acetone | 0.01 | 0.001 |
| Acetal | 0.02 | 0.03 |
| Water | 6 | 7 |

Example 5

A crude ethanol product comprising ethanol, acetic acid, acetaldehyde, water, and ethyl acetate was prepared via acetic acid hydrogenation as discussed above. The crude ethanol product was purified using a separation scheme having distillation columns as shown in FIG. 1C.

The compositions of the residue exiting the fourth column and the distillate exiting the third column are provided in Table 15.

TABLE 15

| Component | Fourth Residue (wt. %) | Third Distillate (wt. %) |
|---|---|---|
| Ethanol | 14.3 | 93.8 |
| Ethyl Acetate | 80.5 | 1.8 |
| Acetaldehyde | — | 0 |
| Acetic Acid | 0.03 | 0.001 |
| Isopropanol | — | 0.005 |
| N-propanol | — | 0 |
| Acetone | 0.01 | 0 |
| Acetal | 0.017 | 0.03 |
| Water | 4.7 | 6.8 |

The third distillate and the fourth residue of Table 15, when combined at a weight ratio of 1.75:1 and 20:1, respectively, provides for a denatured ethanol composition as shown in Table 16.

TABLE 16

| Component | 1.75:1 Weight Ratio wt. % | 20:1 Weight Ratio wt. % |
|---|---|---|
| Ethanol | 64 | 88 |
| Ethyl Acetate | 30 | 5 |
| Acetaldehyde | 0 | 0 |
| Acetic Acid | 0.01 | 0.002 |
| Isopropanol | 0.003 | 0.005 |
| N-propanol | 0 | 0 |
| Acetone | 0 | 0.0005 |
| Acetal | 0.02 | 0.03 |
| Water | 6 | 7 |

Example 6

A crude ethanol product comprising ethanol, acetic acid, acetaldehyde, water, and ethyl acetate was prepared via acetic acid hydrogenation as discussed above. The crude ethanol product was purified using a separation scheme having distillation columns as shown in FIG. 1C.

The compositions of the distillate exiting the fourth column and the distillate exiting the third column are provided in Table 17.

TABLE 17

| Component | Fourth Distillate (wt. %) | Third Distillate (wt. %) |
|---|---|---|
| Ethanol | 5.4 | 93.8 |
| Ethyl Acetate | 39.8 | 1.8 |
| Acetaldehyde | 61.5 | 0 |
| Acetic Acid | 0.02 | 0.001 |
| Isopropanol | — | 0.005 |
| N-propanol | — | 0 |
| Acetone | 0.08 | 0 |
| Acetal | 0.001 | 0.03 |
| Water | 2.1 | 6.8 |

The third distillate and the fourth distillate of Table 17, when combined at a weight ratio of 7:1 and 50:1, respectively, provides for a denatured ethanol compositions as shown in Table 18.

TABLE 18

| Component | 7:1 Weight Ratio wt. % | 50:1 Weight Ratio wt. % |
|---|---|---|
| Ethanol | 80 | 90 |
| Ethyl Acetate | 6 | 2 |

TABLE 18-continued

| Component | 7:1 Weight Ratio wt. % | 50:1 Weight Ratio wt. % |
|---|---|---|
| Acetaldehyde | 7 | 1 |
| Acetic Acid | 0 | 0.001 |
| Isopropanol | 0.004 | 0.005 |
| N-propanol | 0 | 0 |
| Acetone | 0.01 | 0.0015 |
| Acetal | 0.03 | 0.03 |
| Water | 6 | 7 |

Example 7

A crude ethanol product comprising ethanol, acetic acid, acetaldehyde, water, and ethyl acetate was prepared via acetic acid hydrogenation as discussed above. The crude ethanol product was purified using a separation scheme having distillation columns as shown in FIG. 1A.

The compositions of the distillate exiting the first column and the distillate exiting the third column are provided in Table 19.

TABLE 19

| Component | First Distillate (wt. %) | Third Distillate (wt. %) |
|---|---|---|
| Ethanol | 57.6 | 93.8 |
| Ethyl Acetate | 15.1 | 1.8 |
| Acetaldehyde | 1.8 | 0 |
| Acetic Acid | 0.08 | 0.001 |
| Isopropanol | — | 0.005 |
| N-propanol | — | 0 |
| Acetone | 0.01 | 0 |
| Acetal | 0.1 | 0.03 |
| Water | 24.7 | 6.8 |

The third distillate and the first distillate of Table 19, when combined at a weight ratio of 0.05:1 and 3:1, respectively, provides for a denatured ethanol compositions as shown in Table 20.

TABLE 20

| Component | 0.05:1 Weight Ratio wt. % | 3:1 Weight Ratio wt. % |
|---|---|---|
| Ethanol | 60 | 83 |
| Ethyl Acetate | 15 | 5 |
| Acetaldehyde | 2 | 0 |
| Acetic Acid | 0.08 | 0.02 |
| Isopropanol | 0 | 0.004 |
| N-propanol | 0 | 0 |
| Acetone | 0.01 | 0.0025 |
| Acetal | 0.1 | 0.05 |
| Water | 24 | 11 |

Example 8

A crude ethanol product comprising ethanol, acetic acid, acetaldehyde, water, and ethyl acetate was prepared via acetic acid hydrogenation as discussed above. The crude ethanol product may be purified using a first column. In this separation scheme, however, the first distillate may be conveyed directly to the third column, thus bypassing the second and/or fourth columns. The third column may provide a residue and a distillate. The compositions of the first distillate and the third distillate is provided in Table 24. The third distillate is a denatured ethanol composition that may be advantageously prepared without the need for a second column or a fourth column.

TABLE 24

| Component | First Distillate (wt. %) | Third Distillate (wt. %) |
|---|---|---|
| Ethanol | 57.6 | 77 |
| Ethyl Acetate | 15.1 | 20 |
| Acetaldehyde | 1.8 | 2 |
| Acetic Acid | 0.08 | 0 |
| Isopropanol | — | 0 |
| N-propanol | — | 0 |
| Acetone | 0.01 | 0.01 |
| Acetal | 0.1 | 0.13 |
| Water | 24.7 | 0 |

Example 9

A crude ethanol product comprising ethanol, acetic acid, acetaldehyde, water, and ethyl acetate was prepared via acetic acid hydrogenation as discussed above. The crude ethanol product was purified using a separation scheme having, inter alia, first and second distillation columns as shown in FIG. 1A.

Residue from the second column was collected from several runs and introduced to the third column, a 2 inch Oldershaw containing 50 trays, at a rate of 18 g/min. The third column was operated at a temperature of 102° C. at atmospheric pressure. The column differential pressure between the trays in the third column was 6.2 KPa. The third residue was withdrawn at a flow rate of 13 g/min. The third distillate was condensed and refluxed at a 3:2 ratio at the top of the third column.

Figure 2:
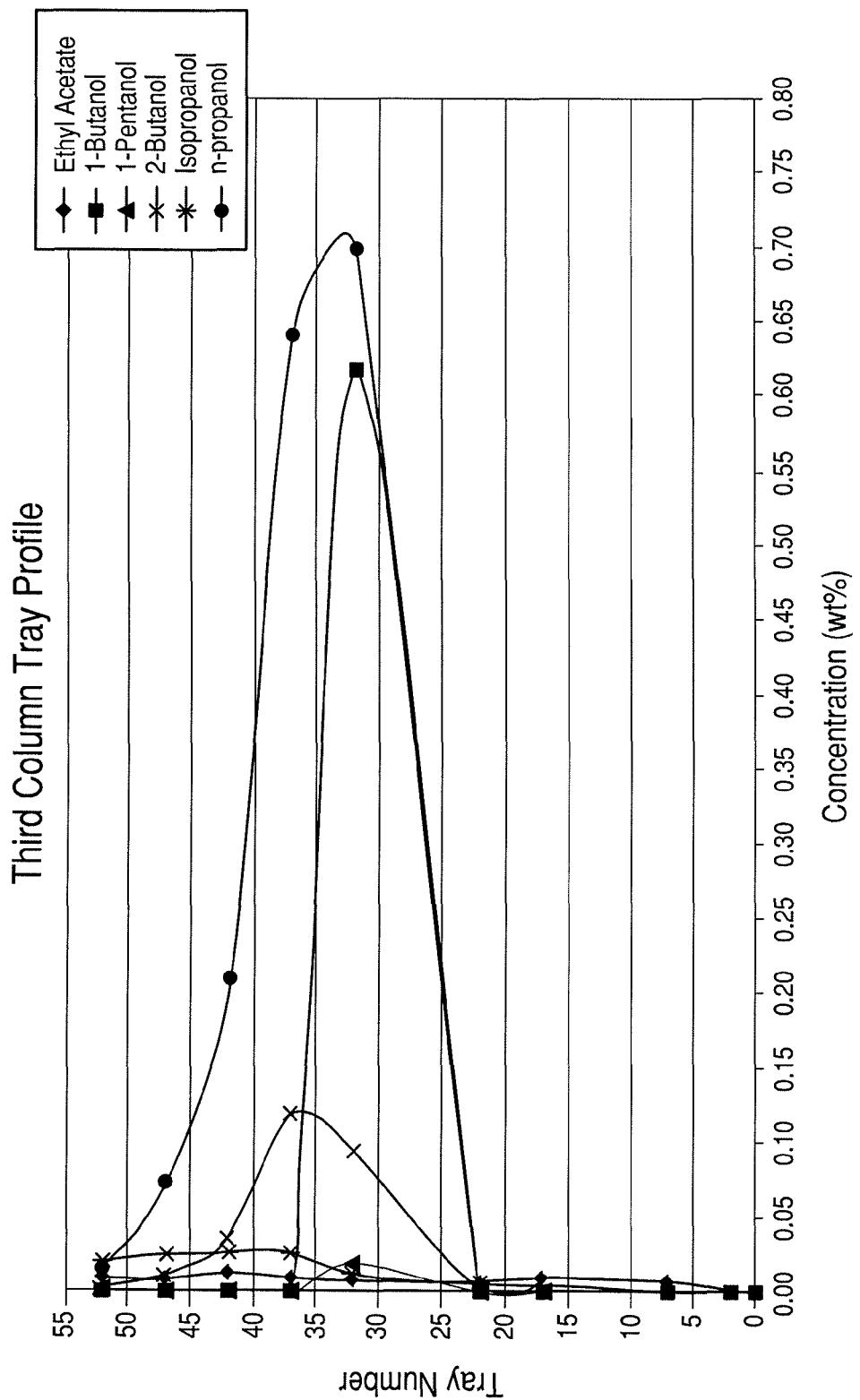
FIG. 2 is a graph showing the composition of an exemplary second residue stream at various tray positions within a third column.

The composition of some components in the second residue stream at various tray positions within the third column is shown in FIG. 2. Ethanol is also present in a significant amount at each tray.

As shown in FIG. 2, a side stream may be withdrawn from the third column. Preferably, the withdrawn side stream comprises ethanol and n-propanol. The side stream withdrawn from the third column provides a denatured ethanol composition comprising ethanol and n-propanol. In some embodiments, the side stream may be combined with a purified ethanol stream, e.g., the third distillate, to form a separate denatured ethanol composition. Each of these denatured ethanol compositions, surprisingly and unexpectedly, may be prepared without the addition of outside denaturant.

In the sample of FIG. 2, the side stream may be withdrawn at from tray 22 to 52, e.g., from tray 25 to tray 43; from tray 25 to tray 40; or from tray 26 to tray 39. The sample of FIG. 2 is, however, merely exemplary. It is within the scope of the invention to adjust the position from which the side stream is withdrawn, based on process parameters, to achieve a desired side stream composition.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing a denatured ethanol composition, the process comprising:
    hydrogenating an acetic acid feed in the presence of a catalyst to form a crude ethanol product comprising ethanol and at least one denaturant;
    separating, in a first column, at least a portion of the crude ethanol product into a first distillate comprising ethanol, acetaldehyde, and ethyl acetate, and a first residue comprising acetic acid;
    recovering the denatured ethanol composition from the first distillate; wherein the denatured ethanol composition comprises from 0.01 wt. % to 40 wt % denaturant, based on the total weight of the denatured ethanol composition.

2. The process of claim 1, wherein the denatured ethanol composition comprises from 50 wt. % to 99 wt. % ethanol.

3. The process of claim 1, wherein the at least one denaturant comprises ethyl acetate.

4. The process of claim 1, wherein the at least one denaturant comprises acetaldehyde.

5. The process of claim 1, wherein the at least one denaturant comprises isopropanol.

6. The process of claim 1, wherein the at least one denaturant comprises diethyl ether.

7. The process of claim 1, wherein the at least one denaturant comprises acetic acid.

8. The process of claim 1, wherein the at least one denaturant is selected from the group consisting of acetaldehyde, acetaldol, ethyl ether, and methanol.

9. The process of claim 1, wherein the crude ethanol product further comprises:
    from 0.01 wt. % to 20 wt. % ethyl acetate;
    from 0.01 wt. % to 10 wt. % acetaldehyde;
    from 0.01 wt. % to 10 wt. % isopropanol;
    from 0.01 wt. % to 20 wt. % diethyl ether;
    from 0 wt. % to 90 wt. % acetic acid; and
    from 5 wt. % to 35 wt. % water, based on the total weight of the crude ethanol product.

10. The process of claim 1, wherein the acetic acid feed comprises acetic acid and acetone, and the at least one denaturant comprises isopropanol.

11. The process of claim 10, further comprising contacting acetic acid and hydrogen, in an auxiliary reactor, under conditions effective to form the acetone.

12. The process of claim 10, wherein the denatured ethanol composition, as formed, comprises from 0.1 wt. % to 10 wt % isopropanol, based on the total weight of the denatured ethanol composition.

13. The process of claim 1, wherein the separating and recovering comprise:
    separating a first portion of the crude ethanol product into the first distillate and the first residue;
    purifying the first distillate to form a purified ethanol stream; and
    combining a second portion of the crude ethanol product with the purified ethanol stream to form the denatured ethanol composition.

14. The process of claim 1, wherein the separating and recovering comprise:
    separating at least a portion of the crude ethanol product into a first distillate and the first residue;
    purifying the first distillate to form a purified ethanol stream; and combining at least a portion of the acetic acid feed with the purified ethanol stream to form the denatured ethanol composition.

15. The process of claim 1, wherein the recovering comprises:
separating at least a portion of the first distillate into an ethanol stream and a denaturant stream comprising acetaldehyde and ethyl acetate;
purifying the ethanol stream to form a purified ethanol stream; and
combining at least a portion of the denaturant stream and the purified ethanol stream to form the denatured ethanol composition.

16. The process of claim 1, further comprising:
separating at least a portion of the first distillate into an ethanol stream;
purifying the ethanol stream to form a purified ethanol stream; and
combining at least a portion of the first residue and the purified ethanol stream to form the denatured ethanol composition.

17. The process of claim 1, wherein the recovering comprises:
separating, in a second column, at least a portion of the first distillate into a second distillate comprising ethyl acetate and/or acetaldehyde, and an ethanol stream;
purifying the ethanol stream to form a purified ethanol stream; and
combining at least a portion of the second distillate and the purified ethanol stream to form the denatured ethanol composition.

18. The process of claim 17, wherein the second column is an extractive distillation column.

19. The process of claim 1, wherein the recovering comprises:
separating, in a second column, at least a portion of the first distillate into a second residue comprising ethyl acetate, and an ethanol stream;
purifying the ethanol stream to form a purified ethanol stream; and
combining at least a portion of the second residue and the purified ethanol stream to form the denatured ethanol composition.

20. The process of claim 19, wherein the second column is-a non-extractive distillation column.

21. The process of claim 1, further comprising:
separating, in a second column, at least a portion of the first distillate into a second residue comprising ethyl acetate, and an ethanol stream;
separating, in a third column, at least a portion of the second residue into a third distillate comprising ethyl acetate and ethanol.

22. The process of claim 1, wherein the denaturant comprises ethyl acetate, and wherein the denatured ethanol composition further comprises:
from 0.01 wt. % to 40 wt. % ethyl acetate;
from 50 wt. % to 99 wt. % ethanol; and
from 1 wt. % to 35 wt. % water, based on the total weight of the denatured ethanol composition.

23. The process of claim 1, wherein the denaturant comprises acetaldehyde, and wherein the denatured ethanol composition further comprises:
from 0.01 wt. % to 10 wt. % acetaldehyde;
from 50 wt. % to 99 wt. % ethanol; and
from 1 wt. % to 35 wt. % water, based on the total weight of the denatured ethanol composition.

24. The process of claim 1, wherein the denaturant comprises isopropanol, and wherein the denatured ethanol composition further comprises:

from 0.1 wt. % to 10 wt. % isopropanol;
from 50 wt. % to 99 wt. % ethanol; and
from 1 wt. % to 35 wt. % water, based on the total weight of the denatured ethanol composition.

25. The process of claim 1, wherein the denaturant comprises diethyl ether, and wherein the denatured ethanol composition further comprises:
from 0.1 wt. % to 20 wt. % diethyl ether;
from 50 wt. % to 99 wt. % ethanol; and
from 1 wt. % to 35 wt. % water, based on the total weight of the denatured ethanol composition.

26. The process of claim 1, wherein the denaturant comprises acetic acid, and wherein the denatured ethanol composition further comprises:
from 0.01 wt. % to 20 wt. % acetic acid from 50 wt. % to 99 wt. % ethanol; and
from 1 wt. % to 35 wt. % water, based on the total weight of the denatured ethanol composition.

27. The process of claim 1, wherein the denaturant comprises n-propanol, and wherein the denatured ethanol composition further comprises:
from 0.1 wt. % to 10 wt. % n-propanol
from 50 wt. % to 99 wt. % ethanol; and
from 1 wt. % to 35 wt. % water, based on the total weight of the denatured ethanol composition.

28. A denatured ethanol composition formed by the process of claim 1.

29. A fuel composition comprising the denatured ethanol composition of claim 28.

30. A process for producing a denatured ethanol composition, the process comprising:
hydrogenating an acetic acid feed in the presence of a catalyst to form a crude ethanol product comprising ethanol and at least one denaturant selected from the group consisting of acetaldehyde and ethyl acetate;
separating at least a portion of the crude ethanol product to form a first denatured ethanol composition comprising ethanol and at least one denaturant selected from the group consisting of acetaldehyde and ethyl acetate and one or more derivative streams comprising acetic acid and water; and
separating at least a portion of the first denatured ethanol composition to form an ethanol stream;
purifying the ethanol stream to form a purified ethanol stream; and
combining at least a portion of the one or more derivative streams and the purified ethanol stream to form a second denatured ethanol composition.

31. A process for producing a denatured ethanol composition, the process comprising:
hydrogenating an acetic acid feed comprising acetic acid and propionic acid in the presence of a catalyst to form a crude ethanol product comprising ethanol and n-propanol and at least one denaturant;
separating, in a first column, at least a portion of the crude ethanol product into a first distillate comprising ethanol, acetaldehyde, ethyl acetate, and n-propanol, and a first residue comprising acetic acid;
separating, in a second column, at least a portion of the first distillate into a second distillate and a second residue comprising ethanol, at least a portion of the n-propanol, and water; and
separating, in a third column, at least a portion of the second residue into a third distillate comprising ethanol and a third residue comprising water; and
recovering the denatured ethanol composition from the third distillate.

32. The process of claim 31, further comprising:
withdrawing, from the third column, a side stream comprising n-propanol.

* * * * *